US006043221A

United States Patent [19]
Magal et al.

[11] Patent Number: 6,043,221
[45] Date of Patent: Mar. 28, 2000

[54] METHOD FOR PREVENTING AND TREATING HEARING LOSS USING A NEUTURIN PROTEIN PRODUCT

[75] Inventors: Ella Magal, Thousand Oaks; John M. Delaney, Newbury Park, both of Calif.

[73] Assignee: Amgen Inc., Thousand Oaks, Calif.

[21] Appl. No.: 09/106,486

[22] Filed: Jun. 29, 1998

Related U.S. Application Data

[60] Provisional application No. 60/054,184, Jul. 30, 1997.

[51] Int. Cl.$^7$ .............................. A61K 38/00; C07K 5/00; C07K 7/00
[52] U.S. Cl. .............................. 514/12; 530/324; 530/350
[58] Field of Search .............................. 514/12; 530/350, 530/324

[56] References Cited

U.S. PATENT DOCUMENTS

| | | |
|---|---|---|
| 4,518,584 | 5/1985 | Mark et al. . |
| 5,106,627 | 4/1992 | Aebischer et al. . |
| 5,653,975 | 8/1997 | Baetge et al. . |
| 5,658,785 | 8/1997 | Johnson . |
| 5,739,307 | 4/1998 | Johnson et al. ....................... 536/23.51 |

FOREIGN PATENT DOCUMENTS

| | | |
|---|---|---|
| 401384 | 12/1990 | European Pat. Off. . |
| WO 91/10470 | 7/1991 | WIPO . |
| WO 93/06116 | 4/1993 | WIPO . |
| WO 95/26408 | 10/1995 | WIPO . |
| WO 97/08196 | 3/1997 | WIPO . |
| WO 97/19693 | 6/1997 | WIPO . |
| 9730722 | 8/1997 | WIPO .............................. A61K 38/18 |

OTHER PUBLICATIONS

Adams et al. (1989), 'Deafness, Dizziness, and Disorders of Equilibrium', *Principles of Neurology* Ch. 14:226–246.
Aebischer et al. (1991), 'Long–Term Cross–Species Brain Transplantation of a Polymer–Encapsulated Dopamine–Secreting Cell Line', *Exper. Neurol.* 111:269–275.
Apfel et al. (1991), 'Nerve Growth Factor Prevents Toxic Neuropathy in Mice', *Ann. Neurol.* 29:87–90.
Choi–Lundberg et al. (1997), 'Dopaminergic Neurons Protected from Degeneration by GDNF Gene Therapy' *Science* 275:838–841.
Cunningham and Wells (1989), 'High–Resolution Epitope Mapping of hGH–Receptor Interactions by Alanine–Scanning Mutagenesis', *Science* 244:1081–1085.
Dayhoff (1972), *Atlas of Protein Sequence and Structure* 5:124.
Ernfors et al. (1995), 'Complementary Roles of BDNF and NT–3 in Vestibular Auditory Development', *Nueron* 14:1153–1164.
Gao et al. (1995), 'Neurotrophin–4/5 Enhances Survival of Cultured Spiral Ganglion Neurons and Protects Them from Cisplatin Neurotoxicity', *J. Neurosci.* 15(7):5079–5087.
Hefti (1986), 'Nerve Growth Factor Promotes Survival of Septal Cholinergic Neurons After Fimbrial Transections', *Neurosci.* 6:2155–2162.

Hefti (1994), 'Neurotrophic Factor Therapy for Nervous System Degenerative Diseases', *J. Neurobiol.* 25:1418–1435.
Higuchi (1989) 'Using PCR to Engineer DNA', *PCR Technology, Principles and Applications for DNA Amplification* Ch.6:61–70.
Hyman et al. (1991), 'BDNF is a neurotrophic factor for dopaminergic neurons of the substantia nigra', *Nature* 350:230–232.
Kelley (1997), 'Cellular Commitment and Differentiation in the Cochlea: Potential Advances Using Gene Transfer' *Audiol. Neurootol.* 2:50–60.
Knusel et al. (1992), 'Brain–derived Neurotrophic Factor Administration Protects Basal Forebrain Cholinergic but Non Nigral Deopaminergic Neurons from Degenerative Changes after Axotomy in the Adult Rat Brain',*J. Neurosci.* 12(11):4391–4402.
Koliatsos et al. (1993), 'Evidence That Brain–Derived Neurotrophic Factor Is a Trophic Factor for Motor Neurons In Vivo', *Neuron* 10:359–367.
Korsching (1993), 'The Neurotrophic Factor Concept: A Reexamination',*J. Neurosci.* 13(7):2739–2748.
Krieglstein et al. (1995), 'TGF–$\beta$ superfamily members promote survival of midbrain dopaminergic neurons and protect them against MPP$^+$ toxicity', *EMBO J.* 14:736–742.
Lefebvre et al. (1994), 'Neurotrophins affect survival and neuritogenesis by adult injured auditory neurons in vitro', *NeuroReport* 5:865–868.
Lin et al. (1993), 'GDNF: A Glial Cell Line–Derived Neurotrophic Factor for Midbrain Dopaminergic Neurons', *Science* 260:1130–1132.
Lindner et al. (1995), 'Implantation of Encapsulated Catecholamine and GDNF–Producing Cells in Rats with Unilateral Dopamine Depletions and Parkinsonian Symptoms' *Exp. Neuro.* 132:62–76.
Lousteau (1987), 'Increased Spiral Ganglion Cell Survival in Electrically Stimulated, Deafened Guinea Pig Cochleae' *Laryngoscope* 97:836–842.
Malik et al. (1992), 'Polyethylene Glycol (PEG)–modified Granulocyte–Macrophage Colony–stimulating Factor (GM–CSF) with Conserved Biological Activity', *Exp. Hematol.* 20:1028–1035.
Matheson et al. (1995), 'The In Vivo Responses of Neonatal Rat Dorsal Root Ganglion Neurons to Neurotrophins and GDNF', *Soc. Neurosci. Abstr.* 21:544.
Mullins et al. (1990), 'Ophthalmic Preparations', *Remington's Pharmaceutical Sciences*, 18th Ed, Ch. 86:1581–1595.

(List continued on next page.)

*Primary Examiner*—Avis Davenport
*Attorney, Agent, or Firm*—Steven M. Odre; Ron K. Levy; Daniel R. Curry

[57] ABSTRACT

The present invention relates generally to methods for preventing and/or treating injury or degeneration of cochlear hair cells and spiral ganglion neurons by administering a neurturin neurotrophic factor protein product. The invention relates more specifically to methods for treating sensorineural hearing loss.

11 Claims, 5 Drawing Sheets

OTHER PUBLICATIONS

Nadol (1981) 'The Aging Peripheral Hearing Mechanism', *Aging: Communication Proecesses and Disorders* Ch. 4:63–85.

Nadol (1993), 'Hearing Loss', *New England J. of Medicine* 329:1092–1102.

Oppenheim et al. (1995), 'Developing motor neurons rescued from programmed and axotomy–induced cell death by GDNF', *Nature* 373:344–346.

Pfingst, et al. (1981), 'Relation of Psychophysical Data to Histopathology in Monkeys with Cochlear Implants' *Acta Otolaryngol* 92:1–13.

Pirvola et al. (1992), 'Brain–derived neurotrophic factor and neurotrophin 3 mRNAs in the peripheral target fields of developing inner ear ganglia', *Proc. Natl. Acad. Sci. USA* 89:9915–9919.

Poulsen et al. (1994), 'TGFβ2 and TGFβ3 Are Potent Survival Factors for Midbrain Dopaminergic Neurons', *Neuron* 13:1245–1252.

Raphael et al. (1996), 'Adenoviral–mediated gene transfer into guinea pig cochlear cells in vivo' *Neuro Ltrs* 207:137–141.

Schecterson et al. (1994), 'Neurotrophin and neurotrophin receptor mRNA expression in developing inner ear', *Hearing Res.* 73:92–100.

Schuknecht (1974) *Pathology of the Ear* pp. 388–403.

Spoendlin (1984), 'Primary Neurons and Synapses', *Ultrastructural Atlas of the Inner Ear* Ch. 6:133–164.

Staecker, et al. (1995) 'NT–3 combined with CNTF promotes survival of neurons in modiolus–spiral ganglion explants', *Neuroreport*, 6(11):1533–1537.

Staeker, et al. (1996), 'NT–3 and/or BDNF therapy prevents loss of auditory neurons following loss of hair cells' *NeuroReport* 7:889–894.

Tresco et al. (1992), 'Polymer Encapsulated Neurotransmitter Secreting Cells', *ASAIO* 38:17–23.

Trupp et al. (1995), 'Peripheral Expression and Biological Activities of GDNF, a New Neurotrophic Factor for Avian and Mammalian Peripheral Neurons', *J. Cell Biol.* 130:137–148.

Weiss et al. (1997), 'Viral–Mediated Gene Transfer in the Cochlea' *Int. J. Devl Neuroscience* 4/5:577–583.

Wheeler et al. (1994), 'Expression of BDNF and NT–3 mRNA in hair cells of the organ of Corti: Quantitative analysis in developing rats', *Hearing Res.* 73:46–56.

Wilson et al. (1980), 'The Efficacy of Steroids in the Treatment of Idopathic Sudden Hearing Loss', *Arch Otolaryngol* 106:772–776.

Winn et al. (1991), 'Behavioral Recovery following Intrastriatal Implantation of Microencapsulated PC12 Cells', *Exper. Neurol.* 113:322–329.

Yan et al. (1992), 'Brain–derived neurotrophic factor rescues spinal motor neurons from axotomy–induced cell death', *Nature* 360:753–755.

Yan et al. (1995), 'In vivo neurotrophic effects of GDNF on neonatal and adult facial motor neurons', *Nature* 373:341–344.

Zheng, et al. (1995) 'Neurotrophin–4/5, Brain–Derived Neurotrophic Factor, and Neurotrophin–3 Promote Survival of Cultured Vestibular Ganglion Neurons and Protect Them against Neurotoxicity of Ototoxins', *J of Neurobiology*, 18(3):330–340.

Kotzbauer et al., *Nature* vol. 384, Dec. 5, 1996, pp. 467–470.

Figure 1

```
Ala Arg Leu Gly Ala Arg Pro Cys Gly Leu Arg
Glu Leu Glu Val Arg Val Ser Glu Leu Gly Leu
Gly Tyr Ala Ser Asp Glu Thr Val Leu Phe Arg
Tyr Cys Ala Gly Ala Cys Glu Ala Ala Ala Arg
Val Tyr Asp Leu Gly Leu Arg Arg Leu Arg Gln
Arg Arg Arg Leu Arg Arg Glu Arg Val Arg Ala
Gln Pro Cys Cys Arg Pro Thr Ala Tyr Glu Asp
Glu Val Ser Phe Leu Asp Ala His Ser Arg Tyr
His Thr Val His Glu Leu Ser Ala Arg Glu Cys
Ala Cys Val
```

Figure 2

```
            Pro Gly Ala Arg Pro Cys Gly Leu Arg
Glu Leu Glu Val Arg Val Ser Glu Leu Gly Leu
Gly Tyr Thr Ser Asp Glu Thr Val Leu Phe Arg
Tyr Cys Ala Gly Ala Cys Glu Ala Ala Ile Arg
Ile Tyr Asp Leu Gly Leu Arg Arg Leu Arg Gln
Arg Arg Arg Val Arg Arg Glu Arg Ala Arg Ala
His Pro Cys Cys Arg Pro Thr Ala Tyr Glu Asp
Glu Val Ser Phe Leu Asp Val His Ser Arg Tyr
His Thr Leu Gln Glu Leu Ser Ala Arg Glu Cys
Ala Cys Val
```

Figure 3

```
ATG GCA CGT CTG GGT GCT CGT CCG TGT GGT CTG
CGT GAA CTG GAA GTT CGT GTT TCC GAA CTG GGT
CTG GGT TAC GCT TCC GAC GAA ACC GTT CTG TTC
CGT TAC TGT GCA GGT GCT TGT GAA GCA GCT GCA
CGT GTT TAC GAC CTG GGT CTG CGT CGC CTG CGT
CAG CGC CGT CGC CTG CGT CGC GAA CGT GTT CGC
GCA CAG CCG TGT TGC CGT CCG ACC GCA TAC GAA
GAC GAA GTT TCC TTC CTG GAC GCT CAC TCC CGT
TAC CAC ACC GTT CAC GAA CTG TCC GCA CGT CAC
TGT GCG TGT GTT TAA
```

Figure 4

Met ala Arg Leu Gly Ala Arg Pro Cys Gly Leu
Arg Glu Leu Glu Val Arg Val Ser Glu Leu Gly
Leu Gly Tyr Ala Ser Asp Glu Thr Val Leu Phe
Arg Tyr Cys Ala Gly Ala Cys Glu Ala Ala Ala
Arg Val Tyr Asp Leu Gly Leu Arg Arg Leu Arg
Gln Arg Arg Arg Leu Arg Arg Glu Arg Val Arg
Ala Gln Pro Cys Cys Arg Pro Thr Ala Tyr Glu
Asp Glu Val Ser Phe Leu Asp Ala His Ser Arg
Tyr His Thr Val His Glu Leu Ser Ala Arg His
Cys Ala Cys Val

Figure 5

```
Met Gln Arg Trp Lys Ala Ala Ala Leu Ala Ser
Val Leu Cys Ser Ser Val Leu Ser Ile Trp Met
Cys Arg Glu Gly Leu Leu Leu Ser His Arg Leu
Gly Pro Ala Leu Val Pro Leu His Arg Leu Pro
Arg Thr Leu Asp Ala Arg Ile Ala Arg Leu Ala
Gln Tyr Arg Ala Leu Leu Gln Gly Ala Pro Asp
Ala Met Glu Leu Arg Glu Leu Thr Pro Trp Ala
Gly Arg Pro Pro Gly Pro Arg Arg Arg Ala Gly
Pro Arg Arg Arg Arg Ala Arg

Ala Arg Leu Gly Ala Arg Pro Cys Gly Leu Arg
Glu Leu Glu Val Arg Val Ser Glu Leu Gly Leu
Gly Tyr Ala Ser Asp Glu Thr Val Leu Phe Arg
Tyr Cys Ala Gly Ala Cys Glu Ala Ala Ala Arg
Val Tyr Asp Leu Gly Leu Arg Arg Leu Arg Gln
Arg Arg Arg Leu Arg Arg Glu Arg Val Arg Ala
Gln Pro Cys Cys Arg Pro Thr Ala Tyr Glu Asp
Glu Val Ser Phe Leu Asp Ala His Ser Arg Tyr
His Thr Val His Glu Leu Ser Ala Arg Glu Cys
Ala Cys Val
```

METHOD FOR PREVENTING AND TREATING HEARING LOSS USING A NEUTURIN PROTEIN PRODUCT

This application claims the benefit of U.S. Provisional application No. 60/054,184 filed Jul. 30, 1997 which is hereby incorporated by reference.

BACKGROUND OF THE INVENTION

The present invention relates generally to methods for preventing and/or treating injury or degeneration of inner ear sensory cells, such as hair cells and auditory neurons, by administering a neurotrophic factor protein product. The invention relates specifically to methods for preventing and/or treating hearing loss due to variety of causes.

Neurotrophic factors are natural proteins, found in the nervous system or in non-nerve tissues innervated by the nervous system, that function to promote the survival and maintain the phenotypic differentiation of certain nerve and/or glial cell populations (Varon et al., Ann. Rev. Neuroscience, 1:327, 1979; Thoenen et al., Science, 229:238, 1985). Because of this physiological role, certain neurotrophic factors have been found useful in treating the degeneration of certain nerve cells and the loss of differentiated function that results from nerve damage. Nerve damage is caused by conditions that compromise the survival and/or proper function of one or more types of nerve cells, including: (1) physical injury, which causes the degeneration of the axonal processes (which in turn causes nerve cell death) and/or nerve cell bodies near the site of injury, (2) temporary or permanent cessation of blood flow (ischemia) to parts of the nervous system, as in stroke, (3) intentional or accidental exposure to neurotoxins, such as the cancer and AIDS chemotherapeutic agents cisplatinum and dideoxycytidine, respectively, (4) chronic metabolic diseases, such as diabetes or renal dysfunction, or (5) neurodegenerative diseases such as Parkinson's disease, Alzheimer's disease, and Amyotrophic Lateral Sclerosis, which result from the degeneration of specific neuronal populations. In order for a particular neurotrophic factor to be potentially useful in treating nerve damage, the class or classes of damaged nerve cells must be responsive to the factor. It has been established that all neuron populations are not responsive to or equally affected by all neurotrophic factors.

The first neurotrophic factor to be identified was nerve growth factor (NGF). NGF is the first member of a defined family of trophic factors, called the neurotrophins, that currently includes brain-derived neurotrophic factor (BDNF), neurotrophin-3 (NT-3), NT-4/5, and NT-6 (Thoenen, Trends. Neurosci., 14:165–170, 1991; Snider, Cell, 77:627–638, 1994; Bothwell, Ann. Rev. Neurosci., 18:223–253, 1995). These neurotrophins are known to act via the family of trk tyrosine kinase receptors, i.e., trkA, trkB, trkC, and the low affinity p75 receptor (Snider, Cell, 77:627–638, 1994; Bothwell, Ann. Rev. Neurosci., 18:223–253, 1995; Chao et al., TINS 18:321–326, 1995).

Glial cell line-derived neurotrophic factor (GDNF) is a protein identified and purified using assays based upon its efficacy in promoting the survival and stimulating the transmitter phenotype of mesencephalic dopaminergic neurons in vitro (Lin et al., Science, 260:1130–1132, 1993). GDNF is a glycosylated disulfide-bonded homodimer that has some structural homology to the transforming growth factor-beta (TGF-β) super family of proteins (Lin et al., Science, 260:1130–1132, 1993; Krieglstein et al., EMBO J., 14:736–742, 1995; Poulsen et al., Neuron, 13:1245–1252, 1994). GDNF mRNA has been detected in muscle and Schwann cells in the peripheral nervous system (Henderson et al., Science, 266:1062–1064, 1994; Trupp et al., J. Cell Biol., 130:137–148, 1995) and in type I astrocytes in the central nervous system (Schaar et al., Exp. Neurol., 124:368–371, 1993). In vivo, treatment with exogenous GDNF stimulates the dopaminergic phenotype of substantia nigra neurons and restores functional deficits induced by axotomy or dopaminergic neurotoxins in animal models of Parkinson's disease (Hudson et al., Brain Res. Bull., 36:425–432, 1995; Beck et al., Nature, 373:339–341, 1995; Tomac et al., Nature, 373:335–339, 1995; Hoffer et al., Neurosci. Lett., 182:107–111, 1994). Although originally thought to be relatively specific for dopaminergic neurons, at least in vitro, evidence is beginning to emerge indicating that GDNF may have a larger spectrum of neurotrophic targets besides mesencephalic dopaminergic and somatic motor neurons (Yan and Matheson, Nature 373:341–344, 1995; Oppenheim et al., Nature, 373:344–346, 1995; Matheson et al., Soc. Neurosci. Abstr, 21, 544, 1995; Trupp et al., J. Cell Biol., 130:137–148, 1995). In particular, GDNF was found to have neurotrophic efficacy on brainstem and spinal cord cholinergic motor neurons, both in vivo and in vitro (Oppenheim et al., Nature, 373:344–346, 1995; Zurn et al., Neuroreport, 6:113–118, 1994; Yan et al., Nature, 373: 341–344, 1995; Henderson et al., Science, 266:1062–1064, 1994), on retinal neurons, such as photoreceptors and retinal ganglion cells, and on sensory neurons from the dorsal root ganglion.

The neuroepithelial hair cells in the organ of Corti of the inner ear, transduce sound into neural activity, which is transmitted along the cochlear division of the eighth cranial nerve. This nerve consists of fibers from three types of neurons (Spoendlin, H. H. In: Friedmann, I. Ballantyne, J., eds. Ultrastructural Atlas of the Inner Ear; London, Butterworth, pp. 133–164, 1984): 1) afferent neurons, which lie in the spiral ganglion and connect the cochlea to the brainstem. 2) efferent olivocochlear neurons, which originate in the superior olivary complex and 3) autonomic adrenergic neurons, which originate in the cervical sympathetic trunk and innervate the cochlea. In the human, there are approximately 30,000 afferent cochlear neurons, with myelinated axons, each consisting of about 50 lamellae, and 4–6 μm in diameter. This histologic structure forms the basis of uniform conduction velocity, which is an important functional feature. Throughout the length of the auditory nerve, there is a trophic arrangement of afferent fibers, with 'basal' fibers wrapped over the centrally placed 'apical' fibers in a twisted rope-like fashion. Spoendlin (Spoendlin, H. H. In: Naunton, R. F., Fernadex, C. eds. Evoked Electrical Activity in the Auditory Nervous System. London, Academic Press, pp. 21–39, 1978) identified two types of afferent neurons in the spiral ganglion on the basis of morphologic differences: type I cells (95%) are bipolar and have myelinated cell bodies and axons that project to the inner hair cells. Type II cells (5%) are monopolar with unmyelinated axons and project to the outer hair cells of the organ of Corti. Each inner hair cell is innervated by about 20 fibers, each of which synapses on only one cell. In contrast, each outer hair cell is innervated by approximately six fibers, and each fiber branches to supply approximately 10 cells. Within the cochlea, the fibers divide into: 1) an inner spiral group, which arises primarily ipsilaterally and synapses with the afferent neurons to the inner hair cells, and 2) a more numerous outer radial group, which arises mainly contralaterally and synapses directly with outer hair cells. There is a minimal threshold at one frequency, the characteristic or best frequency, but the threshold rises sharply for frequencies above and below this level (Pickles, J. O. In: Introduction to the Physiology of Hearing. London, Academic Press, pp. 71–106, 1982). Single auditory nerve fibers therefore appear to behave as band-pass filters. The basilar membrane vibrates preferentially to different frequencies, at different distances along its length, and the frequency selectivity of each cochlear nerve fiber is similar to that of the inner hair cell to which the fiber is connected. Thus, each cochlear nerve fiber exhibits a turning curve covering a different range of frequencies from its neighboring fiber (Evans, E. F. In: Beagley H. A. ed. Auditory investigation: The Scientific and Technological basis. New York, Oxford University Press, 1979). By this mechanism, complex sounds are broken down into component frequencies (frequency resolution) by the filters of the inner ear.

Hearing loss of a degree sufficient to interfere with social and job-related communications is among the most common chronic neural impairments in the U.S. population. On the basis of health-interview data (Vital and health statistics. Series 10. No. 176. Washington, D.C. (DHHS publication no. (PHS) 90-1504), it is estimated that approximately 4 percent of people under 45 years of age and about 29 percent of those 65 years or over have a handicapping loss of hearing. It has been estimated that more than 28 million Americans have hearing impairment and that as many as 2 million of this group are profoundly deaf (A report of the task force on the National Strategic plan. Bethesda, Md.: National Institute of Health, 1989). The prevalence of hearing loss increases dramatically with age. Approximately 1 per 1000 infants has a hearing loss sufficiently severe to prevent the unaided development of spoken language (Gentile, A. et al., Characteristics of persons with impaired hearing: United States, 1962–1963. Series 10. No. 35. Washington, D.C.: Government printing office, 1967 (DHHS publication no. (PHS) 1000) (Human communication and its disorders: an overview. Bethesda, Md.: National Institutes of health, 1970). More than 360 per 1000 persons over the age of 75 have a handicapping hearing loss (Vital and health statistics. Series 10. No. 176. Washington, D.C. (DHHS publication no. (PHS) 90-1504).

It has been estimated that the cost of lost productivity, special education, and medical treatment may exceed $30 billion per year for disorders of hearing, speech and language (1990 annual report of the National Deafness and other Communication Disorders Advisory Board. Washington, D.C.: Government Printing Office, 1991. (DHHS publication no. (NIH) 91-3189). The major common causes of profound deafness in childhood are genetic disorders and meningitis, constituting approximately 13 percent and 9 percent of the total, respectively (Hotchkiss, D. Demographic aspects of hearing impairment: questions and answers. 2nd ed. Washington, D.C.: Gallaudet University Press, 1989). In approximately 50 percent of the cases of childhood deafness, the cause is unknown, but is likely due to genetic causes or predisposition (Nance W E, Sweeney A. Otolaryngol. Clin. North Am 1975; 8: 19–48).

Impairment anywhere along the auditory pathway, from the external auditory canal to the central nervous system, may result in hearing loss. The auditory apparatus can be subdivided into the external and middle ear, inner ear and auditory nerve and central auditory pathways. Auditory information in humans is transduced from a mechanical signal to a neurally conducted electrical impulse by the action of approximately 15,000 neuroepithelial cells (hair cells) and 30,000 first-order neurons (spiral ganglion cells) in the inner ear. All central fibers of spiral ganglion neurons form synapses in the cochlear nucleus of the pontine brainstem. The number of neurons involved in hearing increases dramatically from the cochlea to the auditory brain stem and the auditory cortex. All auditory information is transduced by only 15,000 hair cells, of which the so-called inner hair cells, numbering 3500, are critically important, since they form synapses with approximately 90 percent of the 30,000 primary auditory neurons. Thus, damage to a relatively few cells in the auditory periphery can lead to substantial hearing loss. Hence, most causes of sensorineural loss can be ascribed to lesions in the inner ear (Nadol, J. B., New England Journal of Medicine, 1993, 329: 1092–1102).

Hearing loss can be on the level of conductivity, sensorineural and central level. Conductive hearing loss is caused by lesions involving the external or middle ear, resulting in the destruction of the normal pathway of airborne sound amplified by the tympanic membrane and the ossicles to the inner ear fluids. Sensorineural hearing loss is caused by lesions of the cochlea or the auditory division of the eight cranial nerve. Central hearing loss is due to lesions of the central auditory pathways. These consist of the cochlear and dorsal olivary nucleus complex, inferior colliculi, medial geniculate bodies, auditory cortex in the temporal lobes and interconnecting afferent and efferent fiber tracts (Adams R. D. and Maurice, V. Eds. in: Principles of Neurology. 1989. McGraw-Hill Information services Company. PP 226–246).

As mentioned previously, at least 50 percent of cases of profound deafness in childhood have genetic causes (Brown, K. S., Med. Clin. North AM. 1969; 53:741–72). If one takes into consideration the probability that genetic predisposition is a major causative factor in presbycusis- or age-related hearing loss which affects one third of the population over 75 years of age (Nadol, J. B. In: Beasley D S, Davis G A, eds. Aging: Communication Processes and Disorders. New York: Grune & Stratton, 1981:63–85), genetic and hereditary factors are probably the single most common cause of hearing loss. Genetic anomalies are much more commonly expressed as sensorineural hearing loss than as conductive hearing loss. Genetically determined sensorineural hearing loss is clearly a major, if not the main cause of sensorineural loss, particularly in children (Nance W E, Sweeney A. Otolaryngol. Clin. North Am 1975; 8: 19–48). Among the most common syndromal forms of sensorineural loss are Waardenburg's syndrome, Alport's syndrome and Usher's syndrome.

A variety of commonly used drugs have ototoxic properties. The best known are the aminoglycoside antibiotics (Lerner, S. A. et al. eds. Aminoglycoside ototoxicity. Boston: Little, Brown, 1981; Smith, C. R. et al. N Engl. J. Med. 1980; 302: 1106–9), loop diuretics (Bosher, S. K., Acta Otolaryngol. (Stockholm) 1980; 90: 4–54), salicylates (Myers, E. N. et al., N Engl. J. Med. 1965; 273:587–90) and antineoplastic agents such as cisplatin (Strauss, (Strauss, M. et al., Laryngoscope 1983; 143:1263 –5). Ototoxicity has also been described during oral or parenteral administration of erythromycin (Kroboth, P. D. et al., Arch. Intern Med. 1983; 1: 169–79; Achweitzer, V. G., Olson, N. Arch. Otolaryngol. 1984; 110:258–60).

Most ototoxic substances cause hearing loss by damaging the cochlea, particularly the auditory hair cells and the stria vascularis, a specialized epithelial organ within the inner ear, that is responsible for the homeostasis of fluids and electrolytes (Nadol, J. B. New England J. Med. 1993, 329: 1092–1102). Secondary neural degeneration may occur many years after an ototoxic event affecting the hair cells. There is evidence that some ototoxic substances may be selectively concentrated within the inner ear, resulting in progressive sensorineural loss despite the discontinuation of systemic administration (Federspil, P. et al., J. Infect. Dis. 1976; 134 Suppl: S200–S205)

Trauma due to acoustic overstimulation is another leading cause of deafness. There is individual susceptibility to trauma from noise. Clinically important sensorineural hearing loss may occur in some people exposed to high-intensity noise, even below levels approved by the Occupational Safety and Health Agency (Osguthorpe, J. D. ed. Washington D.C.: American Academy of Otolaryngology-Head and Neck Surgery Foundation, 1988).

Demyelinating processes, such as multiple sclerosis, may cause sensorineural hearing loss (Noffsinger, D et al., Acta Otolaryngol Suppl (Stockh) 1972; 303:1–63). More recently, a form of immune-mediated sensorineural hearing loss has been recognized (McCabe, B. F. Ann Otol Rhinol Laryngol 1979; 88:585–9). The hearing loss is usually bilateral, is rapidly progressive (measured in weeks and months), and may or may not be associated with vestibular symptoms.

A variety of tumors, both primary and metastatic, can produce either a conductive hearing loss, or a sensorineural hearing loss, by invading the inner ear or auditory nerve (Houck, J. R. et al., Otolaryngol Head Neck Surg 1992; 106:92–7). A variety of degenerative disorders of unknown cause can produce sensorineural hearing loss. Meniere's syndrome (Nadol, J. B. ed. Meniere's disease: pathogenesis, pathophysiology, diagnosis, and treatment. Amsterdam: Kugler & Ghedini 1989), characterized by fluctuating sensorineural hearing loss, episodic vertigo, and tinnitus, appears to be caused by a disorder of fluid homeostasis within the inner ear, although the pathogenesis remains unknown. Sudden idiopathic sensorineural hearing loss (Wilson, W. R. et al., Arch Otolaryngol 1980; 106:772–6), causing moderate-to-severe sensorineural deafness, may be due to various causes, including inner ear ischemia and viral labyrinthitis.

Presbycusis, the hearing loss associated with aging, affects more than one third of persons over the age of 75 years. The most common histopathological correlate of presbycusis is the loss of neuroepithelial (hair) cells, neurons, and the stria vascularis of the peripheral auditory system (Schuknecht H. F. Pathology of the Ear. Cambridge, Mass: Harvard University Press, 1974:415–420). Presbycusis is best understood as resulting from the cumulative effects of several noxious influences during life, including noise trauma, ototoxicity and genetically influenced degeneration.

Certain neurotrophic factors have been shown to regulate neuronal differentiation and survival during development (Korsching S. J. Neurosci. 13:2739–2748,1993) and to protect neurons from injury and toxins in adult (Hefti, Neurosci. 6:2155–2162, 1986; Apfel et al., Ann Neurol 29:87–89, 1991; Hyman et al., Nature 350:230–233, 1991; Knusel et al., J. Neurosci. 12:4391–4402, 1992; Yan et al., Nature, 360:753–755, 1992; Koliatsos et al., Neuron, 10:359–367, 1993). In situ hybridization studies indicate that mRNAs for the neurotrophin receptors TrkB and TrkC are expressed by developing cochleovestibular ganglia (Ylikoski et al., Hear. Res. 65:69–78 1993; Schecterson et al., Hearing Res. 73: 92–100 1994) and that mRNAs for BDNF and NT-3 are found in the inner ear, including the organ of Corti (Pirvola et al., Proc. Natl. Acad. Sci. USA 89: 9915–9919, 1992; Schecterson et al., Hearing Res. 73: 92–100 1994; Wheeler et al., Hearing Res. 73: 46–56, 1994). The physiological role of BDNF and NT-3 in the development of the vestibular and auditory systems was investigated in mice that carry a deleted BDNF and/or NT-3 gene (Ernfors et al., Neuron 14: 1153–1164 1995). In the cochlea, BDNF mutants lost type-2 spiral neurons, causing an absence of outer hair cell innervation. NT-3 mutants showed a paucity of afferents and lost 87 percent of spiral neurons, presumably corresponding to type-1 neurons, which innervate inner hair cells. Double mutants had an additive loss, lacking all vestibular and spiral neurons. The requirement of TrkB and TrkC receptors for the survival of specific neuronal populations and the maintenance of target innervation in the peripheral sensory system of the inner ear was demonstrated by studying mice carrying a germline mutation in the tyrosine kinase catalytic domain of these genes (Schimmang et al., Development, 121: 3381–3391 1995). Gao et al., (J. Neurosci. 15: 5079–5087, 1995) showed survival-promoting potency of NT-4/5, BDNF and NT-3 for rat postnatal spiral ganglion neurons in dissociated cultures and that NT-4/5 protected these neurons from neurotoxic effects of the anti-cancer drug, cisplatin. Also, BDNF and NT-3 have been shown to support the survival of adult rat auditory neurons in dissociated cultures (Lefèbvre et al., Neuroreport 5: 865–868, 1994).

There have been no previous reports of the use of neurturin in the treatment of hearing loss. Since hearing impairment is a serious affliction, the identification of any agent and treatment method that can protect the auditory neurons and hair calls from damage would be of great benefit.

SUMMARY OF THE INVENTION

The present invention provides methods for treating sensorineural hearing loss comprising administering to a subject having a lesion in the inner ear a therapeutically effective amount of a neurturin neurotrophic factor protein product. For example, the hearing loss may be associated with injury or degeneration of neuroepithelial hair cells (cochlear hair cells) or spiral ganglion neurons in the inner ear.

The present invention is based on the discoveries that hair cells respond to neurturin by resisting the toxic effects of ototoxins, such as cisplatin and neomycin, and that auditory neurons also respond to neurturin by resisting the toxic effects of variety of ototoxins, such as for example cisplatin, neomycin, and sodium salicylate. Thus, a therapeutically effective amount neurturin protein product may be administered to promote the protection, survival or regeneration of hair cells and spiral ganglion neurons.

It has also been discovered that lesions or disturbances to the vestibular apparatus may also be treated by administering to a subject having such a lesion or disturbance a therapeutically effective amount of a neurturin protein product. Such lesions may result in dizziness, vertigo or loss of balance.

It is contemplated that such neurturin protein products would preferably include a neurturin protein such as that depicted by the amino acid sequence set forth in the Figures, as well as variants and derivatives thereof. It is also contemplated that such neurturin protein products would include [Met$^{-1}$]neurturin.

According to the invention, the neurturin protein product may be administered parenterally at a dose ranging from about 1 μg/kg/day to about 100 mg/kg/day, typically at a dose of about 0.1 mg/kg/day to about 25 mg/kg/day, and usually at a dose of about 5 mg/kg/day to about 20 mg/kg/day. It is also contemplated that, depending on the individual patient's needs and route of administration, the neurturin protein product may be given at a lower frequency such as weekly or several times per week, rather than daily. It is further contemplated that neurturin protein product may be administered directly into the middle ear or the inner ear. One skilled in the art will appreciate that with such administration of a smaller amount of neurturin protein product may be used, for example, a direct middle ear or inner-ear administration dose in the range of about 1 µg/ear to about 1 mg/ear in a single injection or in multiple injections. Alternatively, if administered topically or orally, a comparatively larger dose may be used.

It is further contemplated that neurturin protein product be administered in combination or conjunction with an effective amount of a second therapeutic agents, such as GDNF, BDNF and NT-3. The invention also provides for the use of neurturin protein product in the manufacture of a medicament or pharmaceutical composition for the treatment of injury or degeneration of hair cells and auditory neurons for the variety of causes of sensorineural hearing loss. Such pharmaceutical compositions include topical, oral or middle and inner ear neurturin protein product formulations or in combination with cochlear implants.

It will also be appreciated by those skilled in the art that the administration process can be accomplished via cell therapy and gene therapy means, as further described below. For example, in a gene therapy means cells have been modified to produce and secrete the neurturin protein product. The cells may be modified ex vivo or in vivo. Numerous additional aspects and advantages of the invention will become apparent to those skilled in the art upon consideration of the following detailed description of the invention which describes presently preferred embodiments thereof.

BRIEF DESCRIPTION OF THE FIGS.

Numerous features and advantages of the present invention will become apparent upon review of the figures, wherein:

FIG. 1 depicts an amino acid sequence (SEQ ID NO: 1) of human neurturin neurotrophic factor.

FIG. 2 depicts an amino acid sequence (SEQ ID NO: 2) of mouse neurturin neurotrophic factor.

FIG. 3 depicts a nucleic acid sequence (SEQ ID NO: 3) encoding a neurturin neurotrophic factor analog.

FIG. 4 depicts an amino acid sequence (SEQ ID NOs: 3 or 4) of a human neurturin neurotrophic factor analog.

FIG. 5 depicts an amino acid sequence (SEQ ID NO: 5) of pre-pro human neurturin neurotrophic factor.

DETAILED DESCRIPTION OF THE INVENTION

The present invention provides a method for preventing and/or treating sensorineural hearing loss by administering a therapeutically effective amount of a neurturin neurotrophic factor protein product. According to one aspect of the invention, methods are provided for treating damaged hair cells and auditory neurons by administering a therapeutically effective amount of neurturin protein product by means of a pharmaceutical composition, the implantation of neurturin-expressing cells, or neurturin gene therapy. The invention may be practiced using a biologically active neurturin protein product, including the proteins represented by the amino acid sequences set forth in FIGS. 1, 2, 4 and 5 (SEQ ID NOs: 1, 2, 3, 4 and 5), including variants and derivatives thereof. In addition to oral, parenteral or topical delivery of the neurturin protein product, administration via cell therapy and gene therapy procedures is contemplated.

The present invention is based on the initial discoveries that neurturin protects hair cells from ototoxin-induced cell death in explant cultures of rat's cochlea and dissociated spiral ganglion neurons from adult rat in culture. It is contemplated that administration of a neurturin protein product will protect hair cells and spiral ganglion neurons from traumatic damage (such as noise trauma and acute or chronic treatments of cisplatin and aminoglycoside antibiotics) or from damage resulting from a lack of neurotrophic factors caused by interruption of transport of the factors from the axon to the cell body. Such treatment is expected to allow hair cells and/or auditory neurons to tolerate intermittent insults from trauma or ototoxins and to slow down the progressive degeneration of the auditory neurons and hair cells that is responsible for hearing loss in pathological conditions such as presbycusis (age-related hearing loss), inherited sensorineural degeneration, and post-idiopathic hearing losses and to preserve the functional integrity of the inner ear. It will also support the auditory neurons for a better and longer performance of cochlear implants.

According to the invention, the neurturin protein product may be administered into the middle ear at a dose ranging from about 1 µg/kg/day to about 100 mg/kg/day, typically at a dose of about 0.1 mg/kg/day to about 25 mg/kg/day, and usually at a dose of about 5 mg/kg/day to about 20 mg/kg/day. A neurturin protein product may be administered directly into the inner ear in cases where invasion of the inner ear is already in place such as in the procedure of cochlear implant or surgeries of the inner ear. In such cases, a smaller amount of neurturin protein product will be administered, for example, from about 1 µg/ear to about 1 mg/ear in a single injection or in multiple injections. In situations where the chronic administration of the protein product is needed, a delivery device such as an Alzet mini-pump may be attached to a cannula the tip of which will be introduced into the middle or inner ear for a continuous release of the protein product. Alternatively, a neurturin protein product may be delivered in the form of ear-drops which will penetrate the tympanic membrane of the Bulla. It is further contemplated that a neurturin protein product may be administered together with an effective amount of a second therapeutic agent for the treatment of auditory neuron degeneration, for example GDNF, BDNF and NT-3 as well as other neurotrophic factors or drugs used in the treatment of various inner ear pathologies. A variety of pharmaceutical formulations and different delivery techniques are described in further detail below.

As used herein, the term "neurturin protein product" includes purified natural, synthetic or recombinant neurturin neurotrophic factor, biologically active neurturin variants (including insertion, substitution and deletion variants), and chemically modified derivatives thereof. Also included are neurturin proteins that are substantially homologous to the human neurturin protein having the amino acid sequence set forth in FIGS. 1 and 4 (SEQ ID NOs: 1, 3 and 4). In addition, chemically modified derivatives of these various proteins are included in the present invention. Neurturin protein products also may exist as homodimers or heterodimers in their biologically active form.

The term "biologically active" as used herein means that the neurturin protein product demonstrates similar neurotrophic properties, but not necessarily all of the same properties, and not necessarily to the same degree, as the neurturin having the amino acid sequence set forth in the Figures, but having at least the activity of promoting the protection, survival or regeneration of hair cells and spiral ganglion neurons. The selection of the particular neurotrophic properties of interest depends upon the use for which the neurturin protein product is being administered.

The term "substantially homologous" as used herein means having a degree of homology to the neurturin protein having the amino acid sequence set forth in FIGS. 1, 2, 4 and 5 (SEQ ID NO: 1, 2, 3, 4 and 5) that is preferably in excess of 70%, most preferably in excess of 80%, and even more preferably in excess of 90% or 95%. For example, the degree of homology between the mouse and the human protein is about 91%, and it is contemplated that preferred mammalian neurturin proteins will have a similarly high degree of homology. The percentage of homology or percent identity is calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972), the disclosure of which is hereby incorporated by reference). Also included as substantially homologous is any neurturin protein product which may be isolated by virtue of cross-reactivity with antibodies to the neurturin of FIGS. 1 or 2 (SEQ ID NO: 1 or 2) or whose genes may be isolated through hybridization with the gene or with segments of the gene encoding the neurturin of FIG. 1 or 2 (SEQ ID NO: 1 or 2).

The neurturin protein products according to this invention may be isolated or generated by a variety of means. Exemplary methods for producing neurturin protein products useful in the present invention are substantially similar to the methods of producing GDNF as described in U.S. application Ser. No. 08/182,183 filed May 23, 1994 and its parent applications; PCT Application No. PCT/US92/07888 filed Sep. 17, 1992, published as WO 93/06116 (Lin et al., Syntex-Synergen Neuroscience Joint Venture); European Patent Application No. 92921022.7, published as EP 610 254; and U.S. application Ser. No. 08/535,681 filed Sep. 28, 1995 ("Truncated Glial Cell-Line Derived Neurotrophic Factor"), the disclosures of which are hereby incorporated by reference.

Neurturin protein products may be chemically or recombinantly synthesized by means known to those skilled in the art, see for example Kotzbauer et al., Nature 384:467–470, 1996. Neurturin protein products are preferably produced via recombinant techniques because such methods are capable of achieving comparatively higher amounts of protein at a greater purity. Recombinant neurturin protein product forms include glycosylated and non-glycosylated forms of the protein, and include but are not limited to protein product expressed in bacterial, mammalian or insect cell systems.

In general, recombinant techniques involve isolating the genes responsible for coding neurturin, cloning the gene in suitable vectors and/or cell types, modifying the gene if necessary to encode a desired variant, and expressing the gene in order to produce the neurturin protein product. Alternatively, a nucleotide sequence encoding the desired neurturin protein product may be chemically synthesized. It is contemplated that a neurturin protein product may be expressed using nucleotide sequences which vary in codon usage due to the degeneracies of the genetic code or allelic variations or alterations made to facilitate production of the protein product by the select cell. Kotzbauer et al., Nature 384:467–470, describes the identification of a mouse cDNA and amino acid sequence and a human cDNA and amino acid sequence for neurturin protein. WO93/06116 describes a variety of vectors, host cells, and culture growth conditions for the expression of GDNF protein product which may also be used to express the neurturin protein product. Additional vectors suitable for the expression of neurturin protein product in *E. coli* are disclosed in published European Patent Application No. EP 0 423 980 ("Stem Cell Factor") published Apr. 24, 1991, the disclosure of which is hereby incorporated by reference.

The molecular weight of purified neurturin indicates that the protein is a disulfide-bonded dimer in its biologically active form. The material isolated after expression in a bacterial system is essentially biologically inactive, and exists as a monomer. Refolding is necessary to produce the biologically active disulfide-bonded dimer. Processes suitable for the refolding and naturation of the neurturin expressed in bacterial systems are substantially similar to those described in WO93/06116. Standard in vitro assays for the determination of neurturin activity are also substantially similar to those determining GDNF activity as described in WO93/06116 and in co-owned, co-pending U.S. application Ser. No. 08/535,681 filed Sep. 28, 1995, and are hereby incorporated by reference.

A. Neurturin Variants

The term "neurturin variants" as used herein includes polypeptides in which one or more amino acids have been deleted from ("deletion variants"), inserted into ("addition variants"), or substituted for ("substitution variants"), residues within the amino acid sequence of neurturin of FIGS. 1, 2, 4 and 5. Such variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made provided that the final molecule possesses neurturin biological activity. An exemplary substitution variant is depicted in FIG. 4.

Mutagenesis techniques for the replacement, insertion or deletion of one or more selected amino acid residues are well known to one skilled in the art (e.g., U.S. Pat. No. 4,518,584, the disclosure of which is hereby incorporated by reference.) There are two principal variables in the construction of variants: the location of the mutation site and the nature of the mutation. In designing neurturin variants, the selection of the mutation site and nature of the mutation may depend on the neurturin characteristic(s) to be modified. The sites for mutation can be modified individually or in series, e.g., by (1) substituting first with conservative amino acid choices and then with more radical selections depending upon the results achieved, (2) deleting the target amino acid residue, or (3) inserting amino acid residues adjacent to the located site. Conservative changes in from 1 to 20 amino acids are preferred. Once the amino acid sequence of the desired neurturin protein product is determined, the nucleic acid sequence to be used in the expression of the protein is readily determined. N-terminal and C-terminal deletion variants may also be generated by proteolytic enzymes.

For neurturin deletion variants, deletions generally range from about 1 to 30 residues, more usually from about 1 to 10 residues, and typically from about 1 to 5 contiguous residues. N-terminal, C-terminal and internal intrasequence deletions are contemplated. Deletions may be introduced into regions of low homology with other TGF-β super family members to modify the activity of neurturin. Deletions in areas of substantial homology with other TGF-β super family sequences will be more likely to modify the neurturin biological activity more significantly. The number of consecutive deletions will be selected so as to preserve the tertiary structure of the neurturin protein product in the affected domain, e.g., cysteine crosslinking. Non-limiting examples of deletion variants include truncated neurturin protein products lacking from one to seven N-terminal amino acids, or variants lacking the C-terminal residue, or combinations thereof.

In a basic embodiment, the truncated neurturin proteins may be represented by the following amino acid sequence wherein the amino acid residue numbering scheme of FIG. 1 is used to facilitate comparison to the human neurturin protein:

$$X\text{-}[Cys^8\text{-}Cys^{101}]\text{-}Y$$

wherein
- $[Cys^8\text{-}Cys^{101}]$ represents the amino acid sequence of $Cys^8$ through $Cys^{101}$ as depicted in FIG. 1 (SEQ ID NO: 1);
- Y represents the zero or one or more carboxy-terminus amino acid residues, for example, $Val^{102}$; and
- X represents zero, a methionine residue or one or more amino-terminus amino acid residues, for example:

P
RP
ARP
GARP
LGARP
RLGARP
ARLGARP

As used herein, the term "truncated neurturin protein product" includes biologically active synthetic or recombinant truncated neurturin proteins, truncated neurturin proteins produced from mature neurturin, biologically active truncated neurturin variants (including insertion, substitution and deletion variants), and chemically modified derivatives thereof. Also included are truncated neurturin proteins that are substantially homologous to the human neurturin protein having the amino acid sequence set forth in FIG. 1 (SEQ ID NO: 1).

For neurturin addition variants, amino acid sequence additions typically include N- and/or C-terminal fusions ranging in length from one residue to polypeptides containing a hundred or more residues, as well as internal intrasequence additions of single or multiple amino acid residues. Internal additions may range generally from about 1 to 10 residues, more typically from about 1 to 5 residues, and usually from about 1 to 3 amino acid residues. Examples of N-terminal addition variants include neurturin with an N-terminal methionyl residue (for example, an artifact of the direct expression of neurturin in bacterial recombinant cell culture), which is designated $[Met^{-1}]$neurturin, and fusion of a heterologous N-terminal signal sequence to the N-terminus of neurturin to facilitate the secretion of mature neurturin from recombinant host cells. Such signal sequences generally will be obtained from, and thus be homologous to, the intended host cell species. Additions may also include amino acid sequences derived from the sequence of other neurotrophic factors, for example, from 1 to 35 N-terminal amino acid residues of the human or rat GDNF proteins. A preferred neurturin protein product for use according to the present invention is the recombinant human $[Met^{-1}]$ neurturin.

Neurturin substitution variants have at least one amino acid residue of the human or mouse neurturin amino acid sequence removed and a different residue inserted in its place. Such substitution variants include allelic variants, which are characterized by naturally-occurring nucleotide sequence changes in the species population that may or may not result in an amino acid change. An example of a substitution variant is depicted in FIG. 4 (SEQ ID NOs: 3 or 4).

Specific mutations of the neurturin amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site. Alternatively, the neurturin amino acid sequence may be modified to add glycosylation sites.

One method for identifying neurturin amino acid residues or regions for mutagenesis is called "alanine scanning mutagenesis" as described by Cunningham and Wells (Science, 244:1081–1085, 1989). In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed neurturin variants are screened for the optimal combination of desired activity and degree of activity.

The sites of greatest interest for substitutional mutagenesis include sites where the amino acids found in neurturin proteins from various species are substantially different in terms of side-chain bulk, charge, and/or hydrophobicity. Other sites of interest are those in which particular residues of neurturin-like proteins, obtained from various species, are identical. Such positions are generally important for the biological activity of a protein. Initially, these sites are substituted in a relatively conservative manner. Such conservative substitutions are shown in Table 1 under the heading of preferred substitutions. If such substitutions result in a change in biological activity, then more substantial changes (exemplary substitutions) are introduced, and/or other additions or deletions may be made, and the resulting products screened for activity.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequences) are expected to produce neurturin protein products having functional and chemical characteristics similar to those of natural neurturin. In contrast, substantial modifications in the functional and/or chemical characteristics of neurturin protein products may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for another. Such substituted residues may be introduced into regions of the neurturin protein that are homologous with other TGF-β super family proteins including GDNF, or into the non-homologous regions of the molecule.

B. Neurturin Derivatives

Chemically modified derivatives of neurturin protein products also may be prepared by one of skill in the art given the disclosures herein. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations.

Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. For polyethylene glycol, the preferred molecular weight ranges from about 2 kDa to about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono-, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., Exp. Hematol., 20:1028–1035, 1992 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the e-amino group of the lysine residues and that of the a-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

The present invention contemplates use of derivatives which are prokaryote-expressed neurturin, or variants thereof, linked to at least one polyethylene glycol molecule, as well as use of neurturin, or variants thereof, attached to one or more polyethylene glycol molecules via an acyl or alkyl linkage.

Pegylation may be carried out by any of the pegylation reactions known in the art. See, for example: Focus on Growth Factors, 3 (2):4–10, 1992; EP 0 154 316, the disclosure of which is hereby incorporated by reference; EP 0 401 384; and the other publications cited herein that relate to pegylation. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol with the neurturin protein or variant. Any known or subsequently discovered reactive PEG molecule may be used to carry out the pegylation of neurturin protein or variant. A preferred activated PEG ester is PEG esterified to N-hydroxysuccinimide. As used herein, "acylation" is contemplated to include without limitation the following types of linkages between the therapeutic protein and a water soluble polymer such as PEG: amide, carbamate, urethane, and the like. See Bioconjugate Chem., 5:133–140, 1994. Reaction conditions may be selected from any of those known in the pegylation art or those subsequently developed, but should avoid conditions of temperature, solvent, and pH that would inactivate the neurturin or variant to be modified.

Pegylation by acylation will generally result in a polypegylated neurturin protein or variant. Preferably, the connecting linkage will be an amide. Also preferably, the resulting product will be substantially only (e.g., >95%) mono-, di- or tri-pegylated. However, some species with higher degrees of pegylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the neurturin protein or variant in the presence of a reducing agent. Pegylation by alkylation can also result in poly-pegylated neurturin protein or variant. In addition, one can manipulate the reaction conditions to favor pegylation substantially only at the a-amino group of the N-terminus of the neurturin protein or variant (i.e., a mono-pegylated protein). In either case of monopegylation or polypegylation, the PEG groups are preferably attached to the protein via a —$CH_2$—NH— group. With particular reference to the —$CH_2$— group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the e-amino groups of the lysine residues and that of the a-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/neurturin protein (or variant) conjugate molecules (meaning neurturin protein or variant to which a polymer molecule has been attached substantially only (i.e., >95%) in a single location). More specifically, if polyethylene glycol is used, the present invention also encompasses use of pegylated neurturin protein or variant lacking possibly antigenic linking groups, and having the polyethylene glycol molecule directly coupled to the neurturin protein or variant.

Thus, it is contemplated that neurturin protein products to be used in accordance with the present invention may include pegylated neurturin protein or variants, wherein the PEG group(s) is (are) attached via acyl or alkyl groups. As discussed above, such products may be mono-pegylated or poly-pegylated (e.g., containing 2–6, and preferably 2–5, PEG groups). The PEG groups are generally attached to the protein at the a- or e-amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol. As used herein, polyethylene glycol is meant to encompass any of the forms of PEG that have been used to derivatize other proteins, such as mono-(C1-C10) alkoxy- or aryloxy-polyethylene glycol.

In general, chemical derivatization may be performed under any suitable condition used to react a biologically active substance with an activated polymer molecule. Methods for preparing a pegylated neurturin protein product will generally comprise the steps of (a) reacting a neurturin protein product with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of a mono-polymer/neurturin protein product conjugate molecule will generally comprise the steps of: (a) reacting a neurturin protein product with a reactive PEG molecule under reductive alkylation conditions, at a pH suitable to permit selective modification of the a-amino group at the amino terminus of the neurturin protein product; and (b) obtaining the reaction product(s).

For a substantially homogeneous population of monopolymer/neurturin protein product conjugate molecules, the reductive alkylation reaction conditions are those which permit the selective attachment of the water soluble polymer moiety to the N-terminus of neurturin protein product. Such reaction conditions generally provide for pKa differences between the lysine amino groups and the a-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal a-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa. The preferred average molecular weight is about 5 kDa to about 50 kDa, particularly preferably about 12 kDa to about 25 kDa. The ratio of water-soluble polymer to neurturin protein product will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any neurturin protein product having an a-amino group at the amino terminus, and provide for a substantially homogenous preparation of monopolymer/neurturin protein product conjugate. The term "monopolymer/neurturin protein product conjugate" is used herein to mean a composition comprised of a single polymer molecule attached to a molecule of a neurturin protein product. The monopolymer/neurturin protein product conjugate preferably will have a polymer molecule located at the N-terminus, but not on lysine amino side groups. The preparation will preferably be greater than 90% monopolymer/neurturin protein product conjugate, and more preferably greater than 95% monopolymer/neurturin protein product conjugate, with the remainder of observable molecules being unreacted (i.e., protein lacking the polymer moiety).

For the present reductive alkylation, the reducing agent should be stable in aqueous solution and preferably be able to reduce only the Schiff base formed in the initial process of reductive alkylation. Preferred reducing agents may be selected from sodium borohydride, sodium cyanoborohydride, dimethylamine borane, trimethylamine borane and pyridine borane. A particularly preferred reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

C. Neurturin Protein Product Pharmaceutical Compositions

Neurturin protein product pharmaceutical compositions typically include a therapeutically effective amount of a neurturin protein product in admixture with one or more pharmaceutically and physiologically acceptable formulation materials selected for suitability with the mode of administration. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial perilymph, possibly supplemented with other materials common in compositions for parenteral administration. Neutral buffered saline or saline mixed with serum albumin are further exemplary vehicles.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the rate of release of neurturin protein product, or for promoting the absorption or penetration of neurturin protein product across the tympanic membrane. Such excipients are those substances usually and customarily employed to formulate dosages for middle-ear administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration.

The optimal pharmaceutical formulations will be determined by one skilled in the art depending upon considerations such as the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the present neurturin proteins, variants and derivatives.

Other effective administration forms, such as middle-ear slow-release formulations, inhalant mists, or orally active formulations are also envisioned. For example, in a sustained release formulation, the neurturin protein product may be bound to or incorporated into particulate preparations of polymeric compounds (such as polylactic acid, polyglycolic acid, etc.) or liposomes. Hylauronic acid may also be used, and this may have the effect of promoting sustained duration in the circulation.

Suitable biodegradable sustained release matrices include gelatin and polymers of, e.g., lactic acid, or collagens, including modified collagens such as atelocollagen, methylated collagen, or succinylated collagen. See, e.g., European Patent Application Publication No. EP 412 554 A2 published Feb. 13, 1991. Other suitable sustained release matrices include copolymers of L-glutamic acid and gamma ethyl-L-glutamate, poly (2-hydroxyethyl-methacrylate), ethylene vinyl acetate, poly-D-(-)-3-hydroxybutrrc acid, other polyesters, hyaluronic acid, or liposomes. The controlled release matrix may be prepared by mixing a GDNF solution or gel with the biodegradable matrix carrier, followed by concentrating and drying the mixture.

It is contemplated that a controlled release composition may be prepared in which the protein is dispersed in preformed porous polymeric microparticles. See PCT Application Publication No. WO 93/15722, published Aug. 19, 1993. The microparticles may be prepared from any suitable polymeric material, such as polyesters, polyamides, polyanhydrides, or polyacrylates, and preferably is a biodegradable polymer, such as polylactic acid, poly-glycolic acid, a copolymer of lactic acid and glycolic acid, or poly{1,3-bis(p-carboxyphenoxy)propane-co-sebacic acid}. The microparticles, which are generally 50 to 400 microns in diameter and are permeated with a network of pores ranging from 0.01 to 1 microns, are loaded with protein by equilibrating them in a suspension or solution of protein. Vacuum or pressure may be applied to facilitate migration of the drug into the microparticles. The microparticles may be dried in air, under vacuum, by controlled evaporative drying, by a flowing inert gas, by freeze drying, or other techniques, and then further processed into desired compositions for injection or implantation.

The neurturin protein product pharmaceutical composition also may be formulated for middle-ear administration, e.g., by tympanic membrane infusion or injection, and may also include slow-release or sustained circulation formulations. Such middle-ear administered therapeutic compositions are typically in the form of a pyrogen-free, middle-ear acceptable aqueous solution comprising the neurturin protein product in a pharmaceutically acceptable vehicle. One preferred vehicle is sterile distilled water.

It is also contemplated that certain formulations containing neurturin protein product may be administered orally. A neurturin protein product which is administered in this fashion may be formulated as an elixir, tablet, capsule or gel and may be formulated with or without those carriers customarily used in the compounding of solid dosage forms. The capsule may be designed to release the active portion of the formulation at the point in the gastrointestinal tract when bioavailability is maximized and pre-systemic degradation is minimized. Additional excipients may be included to facilitate absorption of neurturin protein product. Diluents, flavorings, low melting point waxes, vegetable oils, lubricants, suspending agents, tablet disintegrating agents, and binders may also be employed.

The formulation of topical ear preparations, including middle-ear solutions, suspensions and ointments is well known to those skilled in the art (see Remington's Pharmaceutical Sciences, 18th Edition, Chapter 86, pages 1581–1592, Mack Publishing Company, 1990). Other modes of administration are available, including injections to the middle ear, and methods and means for producing middle-ear preparations suitable for such modes of administration are also well known.

As used in this application, "middle-ear" refers to the space between the tympanic membrane and the inner ear. This location is external to all inner ear tissue and an invasive procedure might not be required to access this region if a formulation is developed so that the neurturin will penetrate through the tympanic membrane. Alternatively, the material may be introduced to the middle ear by injection through the tympanic membrane or, in case repeated administrations are needed, a hole will be made in the tympanic membrane. Examples of such systems include inserts and "topically" applied drops, gels or ointments which may be used to deliver therapeutic material to these regions. An opening in the tymapanic membrane is a very frequent procedure done on a office-visit basis, in cases such as infections of the middle ear (usually in children). The opening closes spontaneously after a few days.

In the presently described use of neurturin protein product in the treatment of inner ear disease or injury it is also advantageous that a topically applied formulation include an agent to promote the penetration or transport of the therapeutic agent into the middle and inner ear. Such agents are known in the art. For example, Ke et al., U.S. Pat. No. 5,221,696 disclose the use of materials to enhance the penetration of ophthalmic preparations through the cornea.

Inner-ear systems are those systems which are suitable for use in any tissue compartment within, between or around the tissue layers of the inner-ear, such as the cochlea and vestibular organ. These locations include the different structures of the cochlea such as the stria vascularis, Reissner's membrane, organ of Corti, spiral ligament and the cochlear neurons. An invasive procedure might not be required to access those structures since it has been shown that proteins do penetrate the membrane of the round window into the perilymph of the inner ear.

A particularly suitable vehicle for introducing neurturin into the inner ear by penetration through the round window membrane is artificial perilymph. This solution consists of 10.00 mM D-glucose, 1.5 mM CaCl, 1.5 mM MgCl in a 1.0% solution of Dulbeco's phosphate-buffered saline in deionized water at 280–300 mOsm and pH of 7.2. Yet another preparation may involve the formulation of the neurturin protein product with an agent, such as injectable microspheres or liposomes into the middle ear, that provides for the slow or sustained release of the protein which may then be delivered as a depot injection. Other suitable means for the inner-ear introduction of neurturin protein product includes, implantable drug delivery devices or which contain the neurturin protein product, and a cochlear-implant with a tunnel through, so neurturin can be continuously delivered through it to the inner ear.

The ear-treatment preparations of the present invention, particularly topical preparations, may include other components, for example middle-ear acceptable preservatives, tonicity agents, cosolvents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Sufficient tonicity enhancing agent is advantageously added so that the formulation to be instilled into the ear is compatible with the osmolarity of the endo- and perilymph. Suitable preservatives include, but are not limited to, benzalkonium chloride, thimerosal, phenethyl alcohol, methylparaben, propylparaben, chlorhexidine, sodium benzoate, sorbic acid and the like. Hydrogen peroxide may also be used as preservative. Suitable cosolvents include, but are not limited to, alcohols, glycerin, glycerol, propylene glycol and polyethylene glycol. Suitable complexing agents include caffeine, polyvinylpyrrolidone, beta-cyclodextrin or hydroxypropyl-beta-cyclodextrin. Suitable antioxidants include sodium bisulfite and ascorbic acid. Suitable surfactants or wetting agents are for example sorbitan esters, polysorbates such as polysorbate 80, tromethamine, lecithin, cholesterol, tyloxapal and the like. The buffers can be conventional buffers such as acetate, borate, citrate, phosphate, bicarbonate, or Tris-HCl. Other stabilizing agents may be utilized, including proteins such as serum albumin, gelatin, or immunoglobulins, amino acids such as glycine, glutamate, aspartate, arginine, lysine or cysteine, and mono- and di-saccharides such as glucose, mannose or dextrin.

The formulation components are present in concentration that are acceptable to the middle or inner ear site of administration. For example, buffers are used to maintain the composition at physiological pH or at slightly lower pH, typically within a pH range of from about 5 to about 8.

Additional formulation components may include materials which provide for the prolonged residence of the middle ear administered therapeutic agent so as to maximize the topical contact and promote absorbtion through the round window membrane. Suitable materials include polymers or gel forming materials which provide for increased viscosity of the middle-ear preparation. The suitability of the formulations of the instant invention for controlled release (e.g., sustained and prolonged delivery) of an inner-ear treating agent can be determined by various procedures known in the art. Yet another ear preparation may involve an effective quantity of neurturin protein product in a mixture with non-toxic middle-ear treatment acceptable excipients which are suitable for the manufacture of tablets. By dissolving the tablets in sterile water, or other appropriate vehicle, middle-ear treatment solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia.

Administration/Delivery of Neurturin Protein Product

The neurturin protein product may be administered parenterally via a subcutaneous, intramuscular, intravenous, intraarterial, intranasal, intrapulmonary, intraperitoneal, intraocular, transscleral, intravitreal, subretinal, intrathecal or intracerebral route. In appropriate circumstances, intralesional administration may be indicated, e.g. in irrigation fluid used to wash injured areas or implanted in injured areas with a suitable matrix. Alternatively, neurturin protein product may be administered orally, or into specific areas of the gastrointestinal tract, or via rectal, transdermal or topical routes.

For the treatment of inner-ear conditions, the neurturin protein product may be administered into the middle-ear (or directly into the inner-ear, especially in cases where an invasive procedure means is already in place), by topical application, inserts, injection, implants, cell therapy or gene therapy. For example, slow-releasing implants containing the neurotrophic factor embedded in a biodegradable polymer matrix can deliver neurturin protein product. A neurturin protein product may be administered extracerebrally in a form that has been modified chemically or packaged so that it passes the blood-brain barrier, or it may be administered in connection with one or more agents capable of promoting penetration of neurturin protein product across the barrier. Similarly, the neurturin protein product may be administered in the middle or inner ear, or it may be administered on top of the tympanic membrane in connection with one or more agents capable of promoting penetration or transport of neurturin protein product across the membranes of the ear. The frequency of dosing will depend on the pharmacokinetic parameters of the neurturin protein product as formulated, and the route of administration.

The specific dose may be calculated according to considerations of body weight, body surface area or organ size. Further refinement of the calculations necessary to determine the appropriate dosage for treatment involving each of the above mentioned formulations is routinely made by those of ordinary skill in the art and is within the ambit of tasks routinely performed, especially in light of the dosage information and assays disclosed herein. Appropriate dosages may be ascertained through use of the established assays for determining dosages utilized in conjunction with appropriate dose-response data. It will be appreciated by those skilled in the art that the dosage used in inner-ear administered formulations will be minuscule as compared to that used in a systemic injection or oral administration.

The final dosage regimen involved in a method for treating the above-described conditions will be determined by the attending physician, considering various factors which modify the action of drugs, e.g., the age, condition, body weight, sex and diet of the patient, the severity of any infection, time of administration and other clinical factors. As studies are conducted, further information will emerge regarding the appropriate dosage levels for the treatment of various diseases and conditions.

It is envisioned that the continuous administration or sustained delivery of a neurturin protein product may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the protein which have the effect of continuous presence, in predictable amounts, based on a determined dosage regimen. Thus, neurturin protein products include proteins derivatized or otherwise formulated to effectuate such continuous administration.

Neurturin protein product cell therapy, e.g., middle- or inner ear implantation of cells producing neurturin protein product, is also contemplated. This embodiment would involve implanting into patients cells capable of synthesizing and secreting a biologically active form of neurturin protein product. Such neurturin protein product-producing cells may be cells that are natural producers of neurturin protein product or may be cells which are modified to express the protein. Such modified cells include recombinant cells whose ability to produce a neurturin protein product has been augmented by transformation with a gene encoding the desired neurturin protein product in a vector suitable for promoting its expression and secretion. In order to minimize a potential immunological reaction in patients being administered neurturin protein product of a foreign species, it is preferred that the natural cells producing neurturin protein product be of human origin and produce human neurturin protein product. Likewise, it is preferred that the recombinant cells producing neurturin protein product be transformed with an expression vector containing a gene encoding a human neurturin protein product. Implanted cells may be encapsulated to avoid infiltration of surrounding tissue. Human or non-human animal cells may be implanted in patients in biocompatible, semipermeable polymeric enclosures or membranes that allow release of neurturin protein product, but that prevent destruction of the cells by the patient's immune system or by other detrimental factors from the surrounding tissue. Such an implant, for example, may be attached to the round-window membrane of the middle-ear to produce and release neurturin protein product directly into the perilymph.

The methodology for the membrane encapsulation of living cells is familiar to those of ordinary skill in the art, and the preparation of the encapsulated cells and their implantation in patients may be accomplished without undue experimentation. See, e.g., U.S. Pat. Nos. 4,892,538, 5,011,472, and 5,106,627, each of which is specifically incorporated herein by reference. A system for encapsulating living cells is described in PCT Application WO 91/10425 of Aebischer et al., specifically incorporated herein by reference. See also, PCP Application WO 91/10470 of Aebischer et al., Winn et al., Exper. Neurol., 113 :322–329, 1991, Aebischer et al., Exper. Neurol., 111:269–275, 1991; Tresco et al., ASAIO, 38:17–23, 1992, each of which is specifically incorporated herein by reference. Techniques for formulating a variety of other sustained- or controlled-delivery means, such as liposome carriers, bio-erodible particles or beads and depot injections, are also known to those skilled in the art.

It is also contemplated that the patient's own cells may be transformed ex vivo to produce neurturin protein product and would be directly implanted without encapsulation. For example, organ of Corti supporting cells may be retrieved, the cells cultured and transformed with an appropriate vector and transplanted back into the patient's inner ear where they would produce and release the desired neurturin protein or neurturin protein variant.

Neurturin protein product gene therapy in vivo is also envisioned, by introducing the gene coding for neurturin protein product into targeted inner ear cells via local injection of a nucleic acid construct or other appropriate delivery vectors. (Hefti, J. Neurobiol., 25:1418–1435, 1994). For example, a nucleic acid sequence encoding a neurturin protein product may be contained in an adeno-associated virus vector or adenovirus vector for delivery to the inner ear cells. Alternative viral vectors include, but are not limited to, retrovirus, herpes simplex virus and papilloma virus vectors. Physical transfer, either in vivo or ex vivo as appropriate, may also be achieved by liposome-mediated transfer, direct injection (naked DNA), receptor-mediated transfer (ligand-DNA complex), electroporation, calcium phosphate precipitation or microparticle bombardment (gene gun).

It should be noted that the neurturin protein product formulations described herein may be used for veterinary as well as human applications and that the term "patient" should not be construed in a limiting manner. In the case of veterinary applications, the dosage ranges should be the same as specified above.

Polynucleotides Encoding Neurturin Protein Product

The present invention further provides novel polynucleotides which encode neurturin protein products. When used as a hybridization probe or amplification primer, the nucleic acid sequence will be substantially free from all other nucleic acid sequences. For use in recombinant protein expression, the nucleic acid sequence will generally be substantially free from nucleic acid sequences encoding other proteins, unless a fusion protein is intended. Based upon the present description and using the universal codon table, one of ordinary skill in the art can readily determine all of the nucleic acid sequences which encode the amino acid sequences of a neurturin protein product. It will also be appreciated by those skilled in the art that the novel polynucleotides which encode neurturin protein products include those nucleic acid sequences encoding variant proteins, whether man-made or naturally occurring.

Recombinant expression techniques, conducted in accordance with the descriptions set forth below, may be followed to produce these polynucleotides and express the various neurturin protein products. For example, by inserting a nucleic acid sequence which encodes a protein into an appropriate vector, one skilled in the art can readily produce large quantities of the desired nucleotide sequence. The sequences can then be used to generate detection probes or amplification primers. Alternatively, a polynucleotide encoding a neurturin protein product can be inserted into an expression vector. By introducing the expression vector into an appropriate host, the desired protein may be produced in large amounts.

As further described herein, there are numerous host/vector systems available for the propagation of nucleic acid sequences and/or the production of neurturin protein products. These include, but are not limited to, plasmid, viral and insertional vectors, and prokaryotic and eukaryotic hosts. One skilled in the art can adapt a host/vector system which is capable of propagating or expressing heterologous DNA to produce or express the sequences of the present invention.

By means of such recombinant techniques, the proteins of the present invention are readily produced in commercial quantities. Furthermore, it will be appreciated by those skilled in the art that, in view of the present disclosure, the novel nucleic acid sequences include degenerate nucleic acid sequences encoding the proteins specifically set forth in the Figures, variants of such proteins, and those nucleic acid sequences which hybridize, preferably under stringent hybridization conditions, to complements of these nucleic acid sequences (see, Maniatis et al., Molecular Cloning (A Laboratory Manual); Cold Spring Harbor Laboratory, pages 387 to 389, 1982.) Exemplary stringent hybridization conditions are hybridization in 4×SSC at 62–67° C., followed by washing in 0.1×SSC at 62–67° C. for approximately an hour. Alternatively, exemplary stringent hybridization conditions are hybridization in 45–55% formamide, 4×SSC at 40–45° C. DNA sequences which hybridize to the complementary sequences for neurturin protein under relaxed hybridization conditions and which encode a neurturin protein of the present invention are also included herein. Examples of such relaxed stringency hybridization conditions are 4×SSC at 45–55° C. or hybridization with 30–40% formamide at 40–45° C.

Also provided by the present invention are recombinant DNA constructs involving vector DNA together with the DNA sequence encoding a neurturin protein product. In such DNA constructs, the nucleic acid sequence encoding the protein (with or without signal peptides) is in operative association with a suitable expression control or regulatory sequence capable of directing the replication and/or expression of the protein in a selected host.

Recombinant Expression of a Neurturin Protein Product

Preparation of Polynucleotides Encoding Neurturin Protein Products

A nucleic acid sequence encoding a neurturin protein product, can readily be obtained in a variety of ways, including, without limitation, chemical synthesis, cDNA or genomic library screening, expression library screening, and/or PCR amplification of cDNA. These methods and others useful for isolating such nucleic acid sequences are set forth, for example, by Sambrook et al. (Molecular Cloning: A Laboratory Manual, Cold Spring Harbor Laboratory Press, Cold Spring Harbor, N.Y., 1989), by Ausubel et al., eds (Current Protocols in Molecular Biology, Current Protocols Press, 1994), and by Berger and Kimmel (Methods in Enzymology: Guide to Molecular Cloning Techniques, vol. 152, Academic Press, Inc., San Diego, Calif., 1987).

Chemical synthesis of a nucleic acid sequence which encodes a neurturin protein product can also be accomplished using methods well known in the art, such as those set forth by Engels et al. (Angew. Chem. Intl. Ed., 28:716–734, 1989). These methods include, inter alia, the phosphotriester, phosphoramidite and H-phosphonate methods of nucleic acid sequence synthesis. The nucleic acid sequence encoding the protein will be several hundred base pairs (bp) or nucleotides in length. Large nucleic acid sequences, for example those larger than about 100 nucleotides in length, can be synthesized as several fragments. The fragments can then be ligated together to form a nucleic acid sequence encoding the protein. A preferred method is polymer-supported synthesis using standard phosphoramidite chemistry.

Alternatively, a suitable nucleic acid sequence may be obtained by screening an appropriate cDNA library (i.e., a library prepared from one or more tissue source(s) believed to express the protein) or a genomic library (a library prepared from total genomic DNA). The source of the cDNA library is typically a tissue from any species that is believed to express neurturin in reasonable quantities. The source of the genomic library may be any tissue or tissues from any mammalian or other species believed to harbor a gene encoding neurturin or a neurturin homologue. The library can be screened for the presence of the neurturin cDNA/gene using one or more nucleic acid probes (oligonucleotides, cDNA or genomic DNA fragments that possess an acceptable level of homology to the neurturin or neurturin homologue cDNA or gene to be cloned) that will hybridize selectively with neurturin or neurturin homologue cDNA(s) or gene(s) present in the library. The probes typically used for such library screening usually encode a small region of the neurturin DNA sequence from the same or a similar species as the species from which the library was prepared. Alternatively, the probes may be degenerate, as discussed herein.

Library screening is typically accomplished by annealing the oligonucleotide probe or cDNA to the clones in the library under conditions of stringency that prevent non-specific binding but permit binding of those clones that have a significant level of homology with the probe or primer. Typical hybridization and washing stringency conditions depend in part on the size (i.e., number of nucleotides in length) of the cDNA or oligonucleotide probe, and whether the probe is degenerate. The probability of obtaining a clone(s) is also considered in designing the hybridization solution (i.e., whether a cDNA or genomic library is being screened; if it is a cDNA library, the probability that the cDNA of interest is present at a high level).

Where DNA fragments (such as cDNAs) are used as probes, typical hybridization conditions include those as set forth in Ausubel et al., eds., supra. After hybridization, the blot containing the library is washed at a suitable stringency, depending on several factors such as probe size, expected homology of probe to clone, type of library being screened, number of clones being screened, and the like. Examples of stringent washing solutions (which are usually low in ionic strength and are used at relatively high temperatures) are as follows. One such stringent wash is 0.015 M NaCl, 0.005 M NaCitrate and 0.1% SDS at 55–65° C. Another such stringent buffer is 1 mM $Na_2EDTA$, 40 mM $NaHPO_4$, pH 7.2, and 1% SDS at about 40–50° C. One other stringent wash is 0.2×SSC and 0.1% SDS at about 50–65° C.

There are also exemplary protocols for stringent washing conditions where oligonucleotide probes are used to screen cDNA or genomic libraries. For example, a first protocol uses 6×SSC with 0.05 percent sodium pyrophosphate at a temperature of between about 35 and 62° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where the background non-specific binding appears high. A second protocol uses tetramethylammonium chloride (TMAC) for washing. One such stringent washing solution is 3 M TMAC, 50 mM Tris-HCl, pH 8.0, and 0.2% SDS.

Another suitable method for obtaining a nucleic acid sequence encoding a neurturin protein product is the polymerase chain reaction (PCR). In this method, poly(A)+RNA or total RNA is extracted from a tissue that expresses neurturin. cDNA is then prepared from the RNA using the enzyme reverse transcriptase. Two primers, typically complementary to two separate regions of the neurturin cDNA (oligonucleotides), are then added to the cDNA along with a polymerase such as Taq polymerase, and the polymerase amplifies the cDNA region between the two primers.

Where the method of choice for preparing the nucleic acid sequence encoding the desired neurturin protein product requires the use of oligonucleotide primers or probes (e.g., PCR, cDNA or genomic library screening), the oligonucleotide sequences selected as probes or primers should be of adequate length and sufficiently unambiguous so as to minimize the amount of non-specific binding that will occur during library screening or PCR amplification. The actual sequence of the probes or primers is usually based on conserved or highly homologous sequences or regions from the same or a similar gene from another organism. Optionally, the probes or primers can be fully or partially degenerate, i.e., contain a mixture of probes/primers, all encoding the same amino acid sequence, but using different codons to do so. An alternative to preparing degenerate probes is to place an inosine in some or all of those codon positions that vary by species. The oligonucleotide probes or primers may be prepared by chemical synthesis methods for DNA as described above.

Neurturin protein products based on these nucleic acid sequences, as well as mutant or variant sequences thereof, are also contemplated as within the scope of the present invention. As described above, a mutant or variant sequence is a sequence that contains one or more nucleotide substitutions, deletions, and/or insertions as compared to the wild type sequence and that results in the expression of amino acid sequence variations as compared to the wild type amino acid sequence. In some cases, naturally occurring neurturin amino acid mutants or variants may exist, due to the existence of natural allelic variation. Neurturin protein products based on such naturally occurring mutants or variants are also within the scope of the present invention. Preparation of synthetic mutant sequences is also well known in the art, and is described for example in Wells et al. (Gene, 34:315, 1985) and in Sambrook et al., supra.

Vectors

The cDNA or genomic DNA encoding a neurturin protein product is inserted into a vector for further cloning (amplification of the DNA) or for expression. Suitable vectors are commercially available, or the vector may be specially constructed. The selection or construction of the appropriate vector will depend on 1) whether it is to be used for DNA amplification or for DNA expression, 2) the size of the DNA to be inserted into the vector, and 3) the host cell (e.g., mammalian, insect, yeast, fungal, plant or bacterial cells) to be transformed with the vector. Each vector contains various components depending on its function (amplification of DNA or expression of DNA) and its compatibility with the intended host cell. The vector components generally include, but are not limited to, one or more of the following: a signal sequence, an origin of replication, one or more selection or marker genes, enhancer elements, promoters, a transcription termination sequence, and the like. These components or expression regulatory elements may be obtained from natural sources or synthesized by known procedures. The vectors of the present invention involve a nucleic acid sequence which encodes the neurturin protein product of interest operatively linked to one or more of the following expression control or regulatory sequences capable of directing, controlling or otherwise effecting the expression of the protein by a selected host cell.

Signal Sequence

The signal sequence may be a component of the vector, or it may be a part of the neurturin protein product DNA that is inserted into the vector. The neurturin DNA encodes a signal sequence at the amino terminus of the protein that is cleaved during post-translational processing of the protein to form the mature protein. Included within the scope of this invention are neurturin protein product polynucleotides with the native signal sequence and other pre-pro sequences as well as polynucleotides wherein the native signal sequence is deleted and replaced with a heterologous signal sequence. The heterologous signal sequence selected should be one that is recognized and processed, i.e., cleaved by a signal peptidase, by the host cell. For prokaryotic host cells that do not recognize and process the native neurturin signal sequence, the signal sequence is substituted by a prokaryotic signal sequence selected, for example, from the group of the alkaline phosphatase, penicillinase, or heat-stable enterotoxin II leaders. For yeast secretion, the native neurturin signal sequence may be substituted by the yeast invertase, alpha factor, or acid phosphatase leaders. In mammalian cell expression the native signal sequence is satisfactory, although other mammalian signal sequences may be suitable.

Origin of Replication

Expression and cloning vectors generally include a nucleic acid sequence that enables the vector to replicate in one or more selected host cells. In cloning vectors, this sequence is typically one that enables the vector to replicate independently of the host chromosomal DNA, and includes origins of replication or autonomously replicating sequences. Such sequences are well known for a variety of bacteria, yeasts, and viruses. The origin of replication from the plasmid pBR322 is suitable for most Gram-negative bacteria and various origins (e.g., SV40, polyoma, adenovirus, VSV or BPV) are useful for cloning vectors in mammalian cells. Generally, the origin of replication component is not needed for mammalian expression vectors (for example, the SV40 origin is often used only because it contains the early promoter).

Selection Gene

The expression and cloning vectors typically contain a selection gene. This gene encodes a "marker" protein necessary for the survival or growth of the transformed host cells when grown in a selective culture medium. Host cells that were not transformed with the vector will not contain the selection gene, and therefore, they will not survive in the culture medium. Typical selection genes encode proteins that (a) confer resistance to antibiotics or other toxins, e.g., ampicillin, neomycin, methotrexate, or tetracycline; (b) complement auxotrophic deficiencies; or (c) supply critical nutrients not available from the culture medium.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes a neurturin protein product. As a result, increased quantities of the neurturin protein product are synthesized from the amplified DNA.

For example, cells transformed with the DHFR selection gene are first identified by culturing all of the transformants in a culture medium that contains methotrexate, a competitive antagonist of DHFR. An appropriate host cell when wild-type DHFR is used is the Chinese hamster ovary cell line deficient in DHFR activity (see, for example, Urlaub and Chasin, Proc. Natl. Acad. Sci., USA 77(7): 4216–4220 (1980)). The transformed cells are then exposed to increased levels of methotrexate. This leads to the synthesis of multiple copies of the DHFR gene, and, concomitantly, multiple copies of other DNA present in the expression vector, such as the DNA encoding a neurturin protein.

Promoter

The expression and cloning vectors of the present invention will typically contain a promoter that is recognized by the host organism and operably linked to the nucleic acid sequence encoding the neurturin protein product. Promoters are untranslated sequences located upstream (5') to the start codon of a structural gene (generally within about 100 to 1000 bp) that control the transcription and translation of a particular nucleic acid sequence. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. A large number of promoters, recognized by a variety of potential host cells, are well known. These promoters are operably linked to the DNA encoding neurturin by removing the promoter from the source DNA by restriction enzyme digestion and inserting the desired promoter sequence into the vector. The native neurturin promoter sequence may be used to direct amplification and/or expression of neurturin DNA. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the betalactamase and lactose promoter systems; alkaline phosphatase, a tryptophan (trp) promoter system; and hybrid promoters such as the tac promoter. Other known bacterial promoters are also suitable. Their nucleotide sequences have been published, thereby enabling one skilled in the art to ligate them to the desired DNA sequence(s), using linkers or adaptors as needed to supply any required restriction sites.

Suitable promoting sequences for use with yeast hosts are also well known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, e.g., heat-shock promoters and the actin promoter. A currently used promoter in the production of proteins in CHO cells is SRa. See Takebe et al., Mol. Cell. Biol. 8(1): 466–472 (1988).

Enhancer Element

An enhancer sequence may be inserted into the vector to increase the transcription of a DNA sequence encoding a protein of the present invention by higher eukaryotes. Enhancers are cis-acting elements of DNA, usually about from 10–300 bp in length, that act on the promoter to increase its transcription. Enhancers are relatively orientation and position independent. They have been found 5' and 3' to the transcription unit. Several enhancer sequences available from mammalian genes are known (e.g., globin, elastase, albumin, alpha-fetoprotein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to neurturin DNA, it is typically located at a site 5' from the promoter.

Transcription Termination

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and occasionally 3' untranslated regions of eukaryotic DNAs or cDNAs. These regions contain nucleotide segments transcribed as polyadenylated fragments in the untranslated portion of the mRNA encoding the protein.

The construction of suitable vectors containing one or more of the above-listed components together with the desired neurturin protein product coding sequence is accomplished by standard ligation techniques. Isolated plasmids or DNA fragments are cleaved, tailored, and religated in the desired order to generate the plasmids required. To confirm that the correct sequences have been constructed, the ligation mixtures may be used to transform E. coli, and successful transformants may be selected by known techniques, such as ampicillin or tetracycline resistance as described above. Plasmids from the transformants are then prepared, analyzed by restriction endonuclease digestion, and/or sequenced to confirm the presence of the desired construct.

Vectors that provide for the transient expression of DNA encoding a neurturin protein product in mammalian cells may also be used. In general, transient expression involves the use of an expression vector that is able to replicate efficiently in a host cell, such that the host cell accumulates many copies of the expression vector and, in turn, synthesizes high levels of the desired protein encoded by the expression vector. Transient expression systems, comprising a suitable expression vector and a host cell, allow for the convenient positive identification of proteins encoded by cloned DNAs, as well as for the rapid screening of such proteins for desired biological or physiological properties. Thus, transient expression systems are particularly useful in identifying variants of the protein.

Selection and Transformation of Host Cells

Host cells (e.g., bacterial, mammalian, insect, yeast, or plant cells) transformed with nucleic acid sequences for use in expressing a recombinant neurturin protein are also provided by the present invention. The transformed host cell is cultured under appropriate conditions permitting the expression of the nucleic acid sequence. The selection of suitable host cells and methods for transformation, culture, amplification, screening and product production and purification are well known in the art. See for example, Gething and Sambrook, Nature 293: 620–625 (1981), or alternatively, Kaufman et al., Mol. Cell. Biol., 5 (7): 1750–1759 (1985) or Howley et al., U.S. Pat. No. 4,419,446. The transformed host cell is cultured in a suitable medium, and the expressed factor is then optionally recovered, isolated and purified from the culture medium (or from the cell, if expressed intracellularly) by an appropriate means known to those skilled in the art.

Suitable host cells for cloning or expressing the vectors herein are the prokaryote, yeast, or higher eukaryote cells as described above. Prokaryotic host cells include, but are not limited to, eubacteria, such as Gram-negative or Gram-positive organisms, for example, E. coli, Bacilli such as B. subtilis, Pseudomonas species such as P. aeruginosa, Salmonella typhimurium, or Serratia marcescans. Alternatively, in vitro methods of cloning, e.g., PCR or other nucleic acid polymerase reactions, are suitable.

In addition to prokaryotic host cells, eukaryotic microbes such as filamentous fungi or yeast may be suitable hosts for the expression of neurturin protein products. Saccharomyces cerevisiae, or common baker's yeast, is the most commonly used among lower eukaryotic host microorganisms, but a number of other genera, species, and strains are well known and commonly available.

Suitable host cells for the expression of glycosylated neurturin protein products are derived from multicellular organisms. Such host cells are capable of complex processing and glycosylation activities. In principle, any higher eukaryotic cell culture might be used, whether such culture involves vertebrate or invertebrate cells, including plant and insect cells. Vertebrate cells are generally used as the propagation of vertebrate cells in culture (tissue culture) is a well known procedure. Examples of useful mammalian host cell lines include, but are not limited to, monkey kidney CV1 line transformed by SV40 (COS-7), human embryonic kidney line (293 or 293 cells subcloned for growth in suspension culture), baby hamster kidney cells, and Chinese hamster ovary cells. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of E. coli (e.g., HB101, DH5a, DH10, and MC1061) are well-known as host cells in the field of biotechnology. Various strains of Streptomyces spp. and the like may also be employed. Presently preferred host cells for producing neurturin proteins are bacterial cells (e.g., *Escherichia coli*) and mammalian cells (such as Chinese hamster ovary cells, COS cells, etc.)

The host cells are transfected and preferably transformed with the above-described expression or cloning vectors and cultured in a conventional nutrient medium. The medium may be modified as appropriate for inducing promoters, selecting transformants, or amplifying the genes encoding the desired sequences. Transfection and transformation are performed using standard techniques which are well known to those skilled in the art and which are selected as appropriate to the host cells involved. For example, for mammalian cells without cell walls, the calcium phosphate precipitation method may be used. Electroporation, micro injection and other known techniques may also be used.

Culturing the Host Cells

Transformed cells used to produce proteins of the present invention are cultured in suitable media. The media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamicin), trace elements (defined as inorganic compounds usually present at final concentrations in the micromolar range), and glucose or other energy source. Other supplements may also be included, at appropriate concentrations, as will be appreciated by those skilled in the art. Suitable culture conditions, such as temperature, pH, and the like, are also well known to those skilled in the art for use with the selected host cells.

It is also possible that neurturin protein product may be produced by homologous recombination, or with recombinant production methods utilizing control elements introduced into cells already containing DNA encoding neurturin or GDNF. Homologous recombination is a technique originally developed for targeting genes to induce or correct mutations in transcriptionally active genes (Kucherlapati, Prog. in Nucl. Acid Res. and Mol. Biol. 36:301 (1989)). The basic technique was developed as a method for introducing specific mutations into specific regions of the mammalian genome (Thomas et al., Cell. 44:419–428, 1986; Thomas and Capecchi, Cell. 51:503–512, 1987; Doetschman et al., Proc. Natl. Acad. Sci. 85:8583–8587, 1988) or to correct specific mutations within defective genes (Doetschman et al., Nature. 330:576–578, 1987). Exemplary homologous recombination techniques are described in U.S. Pat. No. 5,272,071 (EP 91 90 3051, EP Publication No. 505 500; PCT/US90/07642, International Publication No. WO 91/09955) the disclosure of which is hereby incorporated by reference.

Through homologous recombination, the DNA sequence to be inserted into the genome can be directed to a specific region of the gene of interest by attaching it to targeting DNA. The targeting DNA is DNA that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize and therefore recombine with other pieces of endogenous DNA through shared homologous regions. If this complementary strand is attached to an oligonucleotide that contains a mutation or a different sequence of DNA, it too is incorporated into the newly synthesized strand as a result of the recombination. As a result of the proofreading function, it is possible for the new sequence of DNA to serve as the template. Thus, the transferred DNA is incorporated into the genome.

If the sequence of a particular gene is known, such as the nucleic acid sequence of a neurturin protein product, the pre-pro sequence or expression control sequence, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA.

In the present invention, attached to these pieces of targeting DNA are regions of DNA which may interact with the expression of a neurturin protein product. For example, a promoter/enhancer element, a suppresser, or an exogenous transcription modulatory element is inserted in the genome of the intended host cell in proximity and orientation sufficient to influence the transcription of DNA encoding the neurturin protein product. The control element does not encode neurturin, but instead controls a portion of the DNA present in the host cell genome. Thus, the expression of the protein may be achieved not by transfection of DNA that encodes the neurturin protein product gene itself, but rather by the use of targeting DNA (containing regions of homology with the endogenous gene of interest) coupled with DNA regulatory segments that provide the endogenous gene sequence with recognizable signals for transcription of a neurturin protein product. In accordance with the present invention, homologous recombination methods may also be used to modify a cell that contains a normally transcriptionally silent neurturin protein product gene to produce a cell which expresses neurturin protein product.

Other aspects and advantages of the present invention will be understood upon consideration of the following illustrative examples. Example 1 addresses the effects of neurturin protein product administration on hair cells in a Cochlea explant culture system. Example 3 addresses the effects of neurturin protein product administration on inner ear auditory neurons (spiral ganglion neurons), in a dissociated cell culture generated from cochlea.

EXAMPLES

Example 1

Neurturin Protein Product Protects Cochlear Hair Cells Against Ototoxicity

Materials

The materials used in the following Example were obtained as follows.

Organ of Corti Dissecting Solution

Dulbecco's Phosphate Buffered Saline (PBS; 1×, without calcium chloride, without magnesium chloride. Cat. #14190-136, Gibco BRL), containing 1.5 g/L D-Glucose (Dextrose. Cat. #15023-021, Gibco BRL).

Organ of Corti Explant Culture Medium

1. High glucose Dulbecco's Modified Eagle Medium (DMEM; 1×, with L-glutamine, without Sodium Pyruvate. Cat. #1 1965-084, Gibco BRL)

2. 0.15 g/100 ml of D-Glucose (Dextrose. Cat. #15023-021, Gibco BRL)
3. 1% N-2 Supplement (100X, Cat. #17502-030, Gibco BRL)
4. 100 Units/ml of Penicillin G, Potassium (Penicillin; Cat. # 21840-020, Gibco BRL)

Methods

Preparation of Medium

DMEM was supplemented with 1% N-2 supplement, and D-glucose was added to a final concentration of 1.5 g/L. Penicillin was added at 100 Units/ml. After mixing, the medium was filtered and kept at 4° C. The medium was prepared fresh just before use in order to minimize inter-experimental variations. Plastic pipettes and containers were used throughout to minimize protein adsorption.

Neurturin Protein Product Solutions

Human recombinant neurturin protein products were prepared as 1 mg/ml solutions in D-PBS (phosphate buffered saline prepared with distilled water) containing five percent bovine serum albumin. The solutions were stored at −85° C. in aliquots. Serial dilutions (0.1; 1; 10; 50; 100 ng/ml in normal culture medium) were prepared in 96 microplates. Ten microliters of ten-fold concentrated neurturin protein product solutions were added to Organ of Corti explant cultures medium containing ototoxins or not (control)(90 $\mu$l). Control cultures received normal medium( 10 $\mu$l). The neurturin protein product treatments were initiated on day of plating. On the second day, media were exchanged into media containing the ototoxins alone, together with neurturin or without both (control).

Dissecting Tools and Culture Dishes

1. The 4" and 5" dissecting forceps and 4" dissecting scissors were from Roboz Surgical, Washington, D.C.
2. Falcon sterile 96-well microplates (Flat Bottom. Cat. #3072), tissue culture plastic ware and polypropylene centrifuge tubes were from Beckton-Dickinson, Lincoln Park, N.J.

Ototoxins and Related Reagents

1. Neomycin solution (Cat. #N1142, Sigma. St. Louis, Mo.), used at a final concentration of 0.6 mM (a fresh solution was made for each experiment by adding 90 $\mu$l of 1 mg/ml neomycin and to 1410 $\mu$l medium).
2. Cisplatin (Platinol-AQ. Cat. #NDC 0015-3220–22, Bristol-Myers Squibb Laboratories, Princeton, N.J.). Used at a final concentration of 35 $\mu$g/ml (a fresh solution was prepared for each experiment by adding 52.5 $\mu$l of 1 mg/ml cisplatin to 1447.5 $\mu$l medium).
3. Triton X-100 (t-Octylphenoxypoly-ethoxyethanol. Cat. #X-100, Sigma. St. Louis, Mo.)
4. Phalloidin (FITC Labeled. Cat. #P-5282, Sigma. St. Louis, Mo.)
5. Vectashield (Mounting Medium, Cat. #H-1000, Vector, Burlingame, Calif.)

Preparation of Rat Organ of Corti Explant

Organ of Corti explants were obtained from P3-P4 Wistar rats. Rats were decapitated, the lower jaw was cut out and skin removed. The temporal bone was collected in dissection solution, the otic capsule exposed and the bony-cartilaginous cochlear capsule was carefully separated from the temporal bone. Freed cochlea were transferred to another Petri dish with dissection solution for further dissection. Intact organs of Corti were obtained by using a fine forceps to hold central VIII nerve tissue and remove it out, then the stria vascular membrane was carefully stripped off, starting from the apex or base. The organ of Corti was then transferred to a 35-mm diameter Petri dish containing cold PBS supplemented with glucose and ready to be cultured.

Cochlea Explant Culture Procedure

Cochlea explants were cultured in uncoated 96 well microplates. A single organ of Corti was placed in a well and was kept floating in the medium.

Explants were kept in normal medium for 24 hours (90 $\mu$l/well). Neurturin protein solution (10 $\mu$l) was added to the 'treated' cultures, and 10 $\mu$l of medium were added to controls. After 24 hours of incubation, the media were changed and the explants were exposed to ototoxin-containing medium (90 $\mu$l), with neurturin protein solution (10 $\mu$l) or without (control). The cultures were incubated for an additional 3 days. The explants were then fixed with 4% paraformaldehyde in 0.1 M D-PBS for 30 minutes at room temperature and processed for immunostaining.

FITC-Phalloidin Staining of Hair Cells

To identify and count hair cells in the organ of Corti, a direct immunostaining method was used to label the actin present naturally in the stereocilia bundles of the hair cells. The explants were washed three times with D-PBS (200 $\mu$l per well) and permeabilized with 1% Triton X-100 in D-PBS for 15 minutes at room temperature. After three washes in D-PBS, the explants were incubated with FITC-labeled Phalloidin (1:60 from stock, 50 $\mu$l/well) for 45 minutes at room temperature. The plates were covered with aluminum foil as the Phalloidin is light sensitive. After three more washes with D-PBS, the labeled explants were placed in a drop of glycerol on a microscope slide, covered with a glass coverslip and sealed with nail polish. The explants were observed under a Nikon Diaphot-300 inverted fluorescence microscope, using FITC filters and fluorescence optics.

Determination of Hair Cell Number

For each experimental point, 2 to 4 cochlea were used. In each cochlea, the number of hair cells was counted in 2–3 section, 175 mm in length each. Only the sections in the middle turn of the cochlea were analyzed. Each experiment was repeated several times. The numbers of hair cells in control and cisplatin- or neomycin-treated cultures was generated from analyzing 40 cochlea per point.

Results

Hair cells in the floating explant cultures did not die during the experiment period of four days. Thus, the number of phalloidin-stained cells present at the end of the 4 days experiment period, in the absence of ototoxins and treatments, was 105.4±6.9 (n=28). Ototoxins added to the explants on the second day post-plating caused significant loss in hair cell number found after 4 days in vitro. Exposure to 35 $\mu$g/ml cisplatin 24 hours after plating caused a loss of about 80 percent of the hair cells: only 20.8%±4.6 (n=21) of the initial number of hair cells survived (Table 1) and after exposure to 0.8 mM neomycin, only 5.9%±4.7 (n=23) of the hair cells survived (Table 2). There was a marked difference in the morphology of the organs of Corti between these two treatments: while the treatment with neomycin resulted in almost complete loss of hair cells, those that were spared were still organized in the typical four row structure (3 rows of outer hair cells and one row of inner hair cells). Cisplatin treatment, on the other hand, caused a marked disruption of the four-row-structure and the surviving cells were randomly located.

In cultures that received neurturin at the time of plating (pretreatment), a significant number of hair cells survived the 3-day exposure to ototoxins (from day 2 to day 4). In cultures exposed to cisplatin, treatment with neurturin concentrations as low as 0.1 ng/ml caused an increase in surviving hair cells from 21% (untreated cultures) to 35%. Maximal protective activity was reached with 1 ng/ml neurturin (50% survival) (Table 1). In cultures exposed to neomycin, neurturin at 0.1 ng/ml increased the number of hair cells from 6% to 22%; maximal neurturin activity (22% survival) was seen with 10 ng/ml neurturin (Table 2). Neurturin treatment preserved the four-row morphology in neomycin-treated cultures, but did not prevent its disruption by cisplatin.

TABLE 1

Effect of neurturin on cochlear hair cells exposed to cisplatin

| | Hair cell survival (% of untreated) |
|---|---|
| Cisplatin alone (35 μg/ml) | 20.8 ± 6.9  n = 28 |
| Cisplatin + Neurturin 0.1 ng/ml | 35.5 ± 9.1  n = 9 |
| Cisplatin + Neurturin 1 ng/ml | 50.0 ± 13.8  n = 5 |
| Cisplatin + Neurturin 10 ng/ml | 37.0 ± 6.1  n = 7 |
| Cisplatin + Neurturin 50 ng/ml | 40.8 ± 5.3  n = 4 |
| Cisplatin + Neurturin 100 ng/ml | 46 ± 10.8  n = 10 |

Neurturin was introduced to the explant cultures on the day of plating. Cisplatin (35 μg/ml) was added 24 hours later, and the cultures were incubated for an additional 3 days. The hair cells were stained with FITC-phalloidin. The number of hair cells was counted in the middle turn of the cochlea in 2–3 sections of 175 μm each. The results are expressed as the percentage of hair cells present in untreated cultures after 4 days in vitro (105.4±6.9; n=28). Each number is the mean ± SD of n cochleas.

TABLE 2

Effect of neurturin on cochlear hair cells exposed to neomycin

| | Hair cell survival (% of untreated) |
|---|---|
| Neomycin alone (0.6 mM) | 5.9 ± 4.7  n = 23 |
| Neomycin + Neurturin 0.1 ng/ml | 21.6 ± 3.1  n = 4 |
| Neomycin + Neurturin 1 ng/ml | 19.0 ± 3.3  n = 3 |
| Neomycin + Neurturin 10 ng/ml | 21.6 ± 5.2  n = 4 |
| Neomycin + Neurturin 50 ng/ml | 17.4 ± 3.9  n = 3 |
| Neomycin + Neurturin 100 ng/ml | 17.0 ± 1.3  n = 3 |

Neurturin was introduced to the explant cultures on the day of plating. Neomycin (35 μg/ml) was added 24 hours later, and the cultures were incubated for an additional 3 days. The hair cells were stained with FITC-phalloidin. The number of hair cells was counted in the middle turn of the cochlea in 2–3 sections of 175 μm each. The results are expressed as the percentage of hair cells present in untreated cultures after 4 days in vitro (105.4±6.9; n=28). Each number is the mean ± SD of n cochleas.

Example 2

Recombinant Production of a Neurturin Protein Product in *E. coli*

Exemplary neurturin protein products, as depicted in the Figures were expressed in *E. coli*. Complementary, overlapping oligonucleotides comprising the encoding nucleotide sequence (e.g., FIG. 3) were synthesized such that the codons used were optimized for *E. coli* expression. The oligonucleotides were annealed and used as templates for PCR procedures as described in PCR Technology, Principles and Applications for DNA Amplification, Henry A. Erlich, ed., Stockton Press, NY, 1989 (Chapter 6, Using PCR to Engineer DNA) the disclosure of which is hereby incorporated by reference. The product of the PCR reaction was the full-length neurturin gene. This DNA fragment was cloned into an expression vector for expression in *E. coli*. Following DNA sequence verification, the expression plasmid was then transformed into an *E. coli* host strain.

Example 3

Neurturin Protein Product to Promote Survival of Inner Ear Auditory Neurons (Spiral Ganglion Neurons) and to Protect Against Ototoxins Materials The materials to be used in the following Example may be obtained as follows.

Cell Culture Media

High glucose Dulbecco's Modified Eagle's Medium (DMEM; #11965-092), Ham's F12 medium (F 12; #11765-021), B27 medium supplement (#17504-010), penicillin/streptomycin (#15070-014), L-glutamine (#25030-016), Dulbecco's phosphate-buffered saline (D-PBS; #14190-052), mouse laminin (#23017-015), bovine serum albumin and fractionV (#110-18-017) are all from GIBCO/BRL, Grand Island, N.Y. Heat-inactivated horse serum is from HyClone, Logan, Utah. Poly-L-omithine hydrobromide (P-3655), bovine insulin (I-5500), human transferrin (T-2252), putrescine (P-6024), progesterone (P-6149) and sodium selenite (S-9133) are all from Sigma Chemical Company, Saint-Louis, Mo. Papain, deoxyribonuclease I (DNAase) and ovalbumin (Papain dissociation system) are from Worthington Biochemicals, Freehold, N.J. Falcon sterile 96-well microplates (#3072), tissue culture plastic ware and polypropylene centrifuge tubes are from Beckton-Dickinson, Oxnard, Calif. Nitex 20 μm nylon mesh (#460) is from Tetko, Elmsford, N.Y. The 4" dissecting forceps and 4" dissecting scissors are from Roboz Surgical, Washington, D.C.

Antibodies and Related Reagents

Neuronal Specific Enolase (NSE) rabbit polyclonal antibody, is from Chemicon (#AB95 1), biotinylated goat anti-rabbit IgG (#BA-1000) and peroxidase-conjugated avidin/biotin complex (ABC Elite; kit PK-6100) are from Vector Laboratories, Burlingame, Calif. 3',3'-diaminobenzidine is from Cappel Laboratories, West Chester, Pa. Superblock blocking buffer in PBS (#37515) is from Pierce, Rockford, Ill. Triton X-100 (X100), Nonidet P-40 (N6507) and hydrogen peroxide (30%, v/v; H1009) are from Sigma. All other reagents are obtained from Sigma Chemical Company (Saint-Louis, Mo.), unless otherwise specified.

Ototoxins

Cisplatin (Platinol-AQ, #NDC 0015-3220-22) is from Bristol-Myers Squibb, Princeton, N.J., sodium salicylate is from J.T. Baker, Phillipsburg, N.J. (#3872-01) and neomycin is from Sigma (#N1 142).

Methods

Preparation of Media

A basal medium is prepared as a 1:1 mixture of DMEM and F12 medium, and is supplemented with B27 medium supplement added as a 50-fold concentrated stock solution. The B27 medium supplement consists of biotin, L-carnitine, corticosterone, ethanolamine, D(+)-galactose, reduced glutathione, linoleic acid, linolenic acid, progesterone, putrescine, retinyl acetate, selenium, T3 (triodo-1-thyronine, DL-alpha-tocopherol; vitamin E), DL-alpha-tocopherol acetate, bovine serum albumin, catalase, insulin, superoxide dismutase and transferrin. L-glutamine is added at a final concentration of about 2 mM, penicillin at about 100 IU/l, and streptomycin at about 100 mg/l. Heat-inactivated horse serum is added to a final concentration of about 2.5 percent, D-glucose is added to a final concentration of about 5 g/l, HEPES buffering agent is added to a final concentration of about 20 mM, bovine insulin is added to a final concentration of about 2.5 mg/ml, and human transferrin is added to a final concentration of about 0.1 mg/ml. After mixing, the pH is adjusted to about 7.3, and the medium is kept at 4° C. The media are prepared fresh just before use in order to minimize inter-experimental variations. Plastic pipettes and containers are used throughout to minimize protein adsorption.

Neurturin Protein Product Solutions

Purified recombinant neurturin protein products (e.g., FIGS. 1 and 3) are prepared as 1 mg/ml solutions in D-PBS (phosphate-buffered saline prepared with distilled water) containing five percent bovine serum albumin. The solutions are stored at –85° C. in aliquots. Serial dilutions are prepared in 96-well microplates. Ten microliters of ten-fold concentrated neurturin protein product solutions are added to cell cultures containing culture medium (90 $\mu$l). Control cultures received D-PBS with 5 percent albumin (10 $\mu$l). The neurturin protein product treatments are added to the cultures one hour after cells are seeded or 24 hours later, alone or together with the ototoxins.

Ototoxins Preparations

Neomycin is added straight from a stock solution (about $10^{-3}$ M) at 10 $\mu$l per well to result in a final concentration of about $10^{-4}$ M. Cisplatin is diluted with culture medium from the stock solution (1 mg/ml) to a solution of 20 $\mu$g/ml and added at 10 $\mu$l per well, to result in a final concentration of 2 $\mu$g/ml. Sodium salicylate is prepared from powder to a stock solution of 1M in PBS and further diluted in the culture medium to 100 mM, which results in a 10 mM final concentration when added at 10 $\mu$l/well to the culture.

Culture Substratum

To encourage optimal attachment of spiral ganglion cells on substratum and neurite outgrowth, the microtiter plate surfaces (the culture substratum) are modified by sequential coating with poly-L-ornithine followed by laminin in accordance with the following procedure. The plate surfaces are completely covered with a 0.1 mg/ml sterile solution of polyornithine in 0.1 M boric acid (pH 8.4) for at least one hour at room temperature, followed by a sterile wash with Super-Q water. The water wash is then aspirated, and a 10 $\mu$g/ml solution of mouse laminin in PBS is added and incubated at 37° C. for two hours. These procedures are conducted just before using the plates in order to ensure reproducibility of the results.

Preparation of Rat Spiral Ganglion Cell Cultures

Three- to four-week-old Wistar rats (obtained from Jackson Laboratories, Bar Harbor, Ma.) are injected with an overdose of the following solution: ketamine (100 mg/ml); Xylazine (20 mg/ml) and Acopromazine Maleate 910 mg/ml) at 3:3:1 proportions. The rats are then killed by decapitation, and the temporal bone with the cochlea are dissected out and transferred sterilely into PBS with 1.5 g/L glucose on ice. A maximum of cochlea are processed per experiment. The cochlea are opened, and the organ of Corti with the bony modiolus is collected into a 50 ml sterile tube containing 5 ml of dissociation medium (120 units papain and 2000 units DNAase in HBSS). The tissue is incubated for 30 minutes at about 37° C. on a rotary platform shaker at about 200 rpm. The dissociation solution is replaced with a fresh solution, and the incubation is resumed for another 30 min. The cells are then dispersed by trituration through fire-polished Pasteur pipettes, sieved through a 40 $\mu$m Nitex nylon mesh to discard undissociated tissue, and centrifuged for five minutes at 200×g using an IEC clinical centrifuge. The resulting cell pellet is resuspended in HBSS containing ovalbumin and about 500 units DNAase, layered on top of a four percent ovalbumin solution (in HBSS) and centrifuged for about 6 minutes at 500×g. The final pellet is resuspended in about 6 ml of the culture medium and seeded at 90 $\mu$l/well in the precoated plates.

Immunohistochemistry of Spiral Ganglion Cells

Spiral ganglion neurons are identified by immunohistochemical staining for neuronal specific enolase (NSE). Cultures of spiral ganglion cells are fixed for about 10 minutes at room temperature with eight percent paraformaldehyde in D-PBS, pH 7.4, added at 100 $\mu$l/well to the culture medium and then replaced by 100 $\mu$l of four percent paraformaldehyde for additional 10 minutes, followed by three washes in D-PBS (200 $\mu$l per 6-mm well). The fixed cultures are then incubated in Superblock blocking buffer in PBS, containing one percent Nonidet P-40 to increase the penetration of the antibody. The rabbit polyclonal anti-NSE antibodies (Chemicon) are then applied at a dilution of 1:6000 in the same buffer, and the cultures are incubated for two hours at 37° C. on a rotary shaker. After three washes with D-PBS, the spiral ganglion cell-bound antibodies are detected using goat-anti-rabbit biotinylated IgG (Vectastain kit from Vector Laboratories, Burlingame, Calif.) at about a 1:300 dilution. The secondary antibody is incubated with the cells for about one hour at 37° C., and the cells are washed three times with D-PBS. The secondary antibody is then labeled with an avidin-biotin-peroxidase complex diluted at 1:300, and the cells are incubated for about 60 minutes at 37° C. After three more washes with D-PBS, the labeled cell cultures are reacted for 5 minutes in a solution of 0.1 M Tris-HCl, pH 7.4, containing 0.04% 3',3'-diaminobenzidine-(HCl)4, 0.06 percent $NiCl_2$ and 0.02 percent hydrogen peroxide.

Determining Spiral Ganglion Cell Survival

After various times in culture (24 hours, 3 days and 4 days), rat spiral ganglion cell cultures are fixed, processed and immunostained for NSE as described above, and the cultures are then examined with bright-light optics at 200× magnification. All of the NSE-positive neurons present in a 6-mm well are counted. Viable spiral ganglion cells are characterized as having a round body with a size ranging from 15–40 $\mu$m and bearing neuritic processes. Spiral ganglion cells showing signs of degeneration, such as having irregular, vacuolated perikarya or fragmented neurites, are excluded from the counts (most of the degenerating spiral ganglion cells, however, detached from the culture substratum). Cell numbers are expressed either as cells/6-mm well or as the fold-change relative to control cell density.

Results

Cultures of rat spiral ganglion neurons may be used to demonstrate the effect of neurturin protein product on survival and protection against ototoxins. The spiral ganglion cells are obtained from three to four-week old rat cochlea. The dissociated cells are then seeded into polyornithine-laminin-coated microplates at a density of about 1 cochlea per 2 wells in DMEM/F12 supplemented with B27 medium supplement, 2.5 percent heat-inactivated horse serum, D-glucose, HEPES, insulin and transferrin. The cultures will consist of a mixture of neurons and non-neuronal cells. Preferably, the only neurons present are spiral ganglion neurons, and these may be identified by the presence of NSE immunoreactivity.

The effect of neurturin protein product administration is assessed on the survival and morphological maturation of cultured rat spiral ganglion neurons, as well as on their ability to resist the toxic effect of a known ototoxin such as cisplatin. Cultures of spiral ganglion cells are treated 24 hours after seeding with human recombinant neurturin protein product (ranging from 50 ng/ml to 0.1 ng/ml) alone, or in combination with cisplatin (35 µg/ml). Twenty four hours after seeding, it is expected that there is no difference in the number of auditory neurons between control cultures and those treated with neurturin at 1 ng/ml and 10 ng/ml. After an additional period of 3 days, treatment with neurturin at a concentration of 1 ng/ml is not expected to result in a significant increase in neuronal cell number. It is envisioned, however, that there will be a marked trophic effect: the neuronal soma are larger and fibers longer and more elaborate than in control cultures. In cultures treated with 10 ng/ml neurturin, about 70% of the neurons present after 24 hours are expected to survive, representing an average 40% increase over control cultures. The trophic effect is expected to be even stronger than in cultures treated with 1 ng/ml neurturin.

Neurturin is also expected to protect spiral ganglion neurons from cisplatin toxicity. Exposure of cultures to 5 µg/ml cisplatin 24 hours after seeding may result in the loss of about 90% of the initial number (at 24 hours) of the neurons after 4 days in culture. When neurturin is added together with the cisplatin, the number of neurons found after 4 days is expected to be significantly higher. It is also envisioned that this protective effect of neurturin is dose-dependent and that about 60 percent of the neurons that respond to neurturin (about 40% of the spiral ganglion neuron population) can also be protected against cisplatin toxicity.

Example 4

Neurturin Protein Product to Promote In vivo Survival of Cochlear Hair Cells The following example describes the inner ear administration of neurturin protein product to protect cochlear hair cells against ototoxicity in an animal model. The neurturin protein product is introduced into the inner ear via a cannula pushed into the scala tympani through a hole drilled in the basal turn of the cochlea. The cannula is connected to an Alzet mini-pump loaded with neurturin protein product (50 ng/ml) at a releasing rate of 0.5 µl/hour for 14 days. Cisplatin i.m. injections are started two days after the cannulation, at either 1 mg/ml daily for 15 days or at 7.5 mg/kg twice, at a 5 days interval. The experiment is terminated after 27 days. The hair cells are stained with FITC-phalloidin, and their number is determined in the middle turn of the cochlea (in at least 20% of the middle turn part). The results are expressed as the percent of hair cells lost for each individual guinea pig for the neurturin protein product treated ear (right ear) and the untreated ear (left ear).

Materials

The materials to be used in the following Example are obtained as follows

Mini-pump Preparation Materials

Medical vinyl tubing size V/4, catalog No BB317-85, is from Bolab Products ((800) 331-7724). Fisher brand 5 ml plastic pipettes are used. Microlumen Polyimide tubing, catalog #8004853 OG (Tampa, Fla.) is used. Silicone Medical Product MDX 4-4210, is from Dow Corning Corporation, Midland, Mich. Alzet osmotic mini-pump flow moderator and Alzet osmotic mini-pump, Catalog No 2002, are from Alza Corp., Palo Alto, Calif. Tape (TimeMed tape). Prosil-28, Product No 11975-0, is from PCR Incorporated, Gainesville Fla. Purified neurturin protein products are prepared as 50 ng/ml solutions in D-PBS and 0.1% BSA. Sterile 0.1% methylene blue (catalog #M-9140) dissolved in PBS, and mineral oil (catalog #400-5), are from Sigma.

Mini-pump Preparation Procedure

Vinyl tubing is cut into an approximately four inch section and placed in a miniature vise. A piece of the Microlumen Polyimide tube (7 mm) is placed into the end of the vinyl tube. Silicone is mixed by adding approximately 10 parts of base and one part of curing agent. A droplet is placed at the opening of the vinyl tube using a fine probe, and the Microlumen tube is pushed into the vinyl, leaving 3.75 mm length extending from the vinyl tube. Using a drop of Silicone on the probe, a small ball is created around the Microlumen tube, 0.5 mm from the tip, and allowed to dry over night.

The diameter of a 5 ml pipette is increased by applying three concentric layers of tape down the length of the pipette. A constant gap is left where the pipette remains uncovered. V/4 tubing is wrapped around the pipette, and the coils are adjusted so that there are two loose ends of tubing and there is a continuous contact between all coils. Two thin strips of tape are aligned with the edges of the tape on the pipette, to secure the coil in place. Two thin lines of super glue are applied evenly on the coils. After drying for a minimum of one hour, the loose ends are aligned approximately parallel to the pipette and secured in place with one strip of tape. A drop of super glue is applied to secure the tubing to the coils. Following overnight drying, the tape is removed and the coils are slid off the pipette. A flow moderator is inserted into one of the loose ends and secured with one drop of super glue.

The coils are flushed with 1% Prosil-28 in water, rinsed thoroughly with water and then flushed with 70% ethanol. The ethanol is removed by means of a syringe or air vacuum. Coils are left in the desiccator with air vacuum on for at least 30 minutes and are kept overnight in the closed and tight desiccator followed by gas sterilization. During the loading procedure, the coil device is kept horizontal as much as possible to prevent gravity driven movement of the liquids of neurturin protein product, oil, and dye. The formation of air bubbles in the pump or coils is avoided. The pump is submerged in sterile PBS and incubated overnight at 37° C.

The loading of a pump with methylene dye is done by holding the pump in a vertical position. A dye-loaded syringe is inserted completely into the pump, and the dye is injected until the pump overflowed. Injection of any air bubbles into the pump is avoided. A short piece of sterile V/4 tubing is placed onto the Flow Moderator. Neurturin protein product is loaded at a concentration of 50 ng/ml in PBS+ 0.1% BSA, in a total volume of 230 µl, to within about 10 mm of the cannula tip, using a syringe connected with V/4 tubing. For vehicle control experiments, the same volume of PBS+0.1% BSA is loaded into the pumps. The short piece of V/4 tubing is removed. Mineral oil is then loaded into the coil device with a syringe in such a way that a 2 mm air space and 7 mm of mineral oil are interposed between the pump fluid and the line fluid (infusion fluid). A Flow Moderator is inserted completely into the pump.

Pump Insertion in Inner Ear

Materials

Tissue adhesive glue—Cyanoacrylate, is from Vetbond Tissue Adhesive, 3M Animal Care Products, St. Paul, Minn. Carboxylate cement ESPE Durelon, catalog #03828, is from ESPE-Premier Sales Corp., Norristown Pa. Methyl methacrylate is from Lang Jet Acrylic, Lang Dental MFG, Co., Wheeling, Ill. Dissecting tools are from Roboz Surgical. Xylazine, ketamine and buprenorphine are used. Lubricant Ophthalmic Ointment (AKWA Tears) is from Akorn Inc., Abita Springs La. Xylocaine 2%, catalog No NDC 0186-0160–01, is from ASTRA. Medical Grade Silicone Grease, Art. No. 51.300, is from Unimed. Durelon Pulver powder carboxylate-cement, catalog No. D-82229, is from ESPE, Seefeld. Sulfate ointment (Bacitracin Zinc-neomycin, catalog No. 0168-0012-31) is from Fougera.

Procedure

Albino guinea pigs (250–350 g) are anesthetized with a mixture of xylazine 10 mg/kg, ketamine 40 mg/kg and buprenorphine 0.05 mg/kg. The right ear area is shaved caudally, starting about 2 cm anterior to vertex, 4–5 cm posterior to scapulae and postauricularly. The shaved area is washed with Betadine. Lubricant ophthalmic ointment is applied to both eyes. Xylocaine is injected subcutaneously into the tissue to be incised. Using aseptic technique, a post-auricular incision is made. Using a fine needle, a hole is drilled into the bulla to expose the middle ear cavity and visualize the cochlea. A small hole is drilled manually into the bone wall of the basal turn, below the round window using a fine needle. The tip of the cannula is inserted into the hole until the silicone drop is seated against the bone, which places the cannula tip about midway into the scala tympani canal. A drop of cyanoacrylate is placed at the bulla hole. Carboxylate cement is placed around the cannula over the cyanoacrylate. Once the cement hardens, the placement is confirmed, and the rest of the hole is covered with carboxylate cement on top of a layer of silicone grease. A subcutaneous pocket is made between the scapulae to accommodate the pump which is then inserted. The subcutaneous pocket is rinsed once with 3 ml of a solution of nitrofurazone dissolved in sterile PBS and is then filed with 3 ml of sterile PBS plus 1% Gentamycin to discourage infection. The incision is closed with wound clips after nitrofurazone powder is applied around the wound.

Deafening

Materials

Cisplatin (Platinol-AQ), catalog No NDC 0015-3220-22, is from Bristol-Myers Squibb Laboratories, Princeton. N.J.

Procedure

Injections of cisplatin (i.p.) are started two days after mini-pump implantation. Two paradigms of application are used: either two 7.5 mg/kg injections made at a 5 days interval, or 1 mg/kg daily, for 15 days.

Perfusion

After four weeks, the guinea pigs are deeply anesthetized with a mixture of xylazine and ketamine, and are perfused transcardially with ice-cold PBS followed by ice-cold 4% paraformaldehyde in PBS. Temporal bones are removed, and the bony cochlea is placed in 4% paraformaldehyde for postfixation overnight at 4° C.

Staining

Surface preparation and Phalloidin staining methods are used to stain hair cells. The bony cochlea is opened by a fine needle or #11 blade. Stria vascularis is removed using a fine forceps. In a petri dish filled with PBS, the basal membrane is carefully dissected out from the boney modiolus, using fine needles. Care is taken to remove it intact. The procedure for Phalloidin staining is similar to that performed for the in vitro explants, with the following changes: permeabilization is done for 20–30 minutes, and Phalloidin is added for 90 minutes. Apex, middle turn and basal turn pieces are mounted on a 60×22 glass coverslip. A drop of VECTASHIELD mounting medium is added, and the samples are covered with a 22×22 mm coverslip and sealed with nail polish to prevent evaporation.

Data Analysis

Each cochlea is examined under microscope with a FITC filter set. Eight segments with the greatest hair cell loss from midturn of basal membrane are selected and photographed using an attached computer printer. Hair cell counts are performed manually, using the photographs. In each animal, hair cell loss in the left ear (as a control, i.e., without neurturin protein product infusion) is compared to hair cell loss in the right ear (neurturin protein product infused).

Results

Cisplatin injections result in a significant loss of hair cells in the cochlea. This loss, in the middle turn sections analyzed in the left ears of three guinea pigs injected with cisplatin at 1 mg/kg daily for 15 days, is expected to be from to 50%. Also in the guinea pig injected with cisplatin at a 7.5 mg/kg twice, instead of the 1 mg/kg daily, there is an anticipated loss of approximately 40% of hair cells in the left ear. The introduction of neurturin into the right inner ear of each of the guinea pigs, is expected to result in a significant reduction in the loss of hair cells. In animals implanted with a mini-pump filed with vehicle instead of neurturin protein product, there is no expected difference in the number of hair cells found in the left ear (untreated ear) and the right ear (implanted) ear.

Example 5

Neurturin Protein Product Injections to Promote In vivo Survival of Cochlear Hair Cells The following example describes the use of neurturin protein products to protect cochlear hair cells against ototoxicity in an animal model when applied into the middle ear. Neurturin protein product is introduced into the right middle ear by a single injection through the tympanic membrane at a concentration of 1 mg/ml in PBS +1% BSA in a volume of 125–135 µl. Cisplatin i.m. injections are started a day after the neurturin protein product injection at 7.5 mg/kg, twice, at a 5 days interval. The experiment is terminated three days after the second cisplatin injection. The hair cells are stained with FITC-phalloidin, and their number determined in the middle turn of the cochlea (in at least 20% of the middle turn part). The results are expressed as the percent of hair cells lost for each individual guinea pig for the neurturin protein product treated ear (right ear) and the untreated (left ear).

Materials

The materials used in this experiment are the same as those used in Example 4.

Procedure

Albino guinea pigs (weighing 600–700 g) are anesthetized with a mixture of xylazine 10 mg/kg, ketamine 40 mg/kg and buprenorphine 0.05 mg/kg. Under a surgical microscope, a hole is made in the tympanic membrane of the right ear by inserting a 27 gauge needle into the membrane. In another location of the tympanic membrane, neurturin protein product (at a concentration of 1 mg/ml in PBS+1% BSA) is injected into the middle ear cavity so that the whole cavity is full (125–135 µl). A few animals are injected with vehicle only (PBS+0.1% BSA) instead of neurturin protein product. The next day, an i.m. injection of cisplatin (7.5 mg/kg) is made. Five days later, a second injection at the same concentration is made. Three days later (8 days of total experiment period), the animals are sacrificed, tissues are fixed and cochlea are analyzed as described in Example 4.

Results

At eight days, the guinea pigs injected with cisplatin are expected to display a significant loss of hair cells in the cochlea. In the left ears, the ears that do not receive neurturin protein product, the loss of hair cells in the middle turn of the cochlea is expected to be 35 to 50%. Injection of neurturin protein product into the cavity of the right middle ear, at 1 mg/ml, is expected to reduce this loss significantly: to about 16 to 30%. Guinea pigs that receive vehicle injections into the right ear instead of neurturin protein product, are not expected to demonstrate a difference in hair cell number between the right (treated) and left (untreated) ear.

Numerous modifications and variations in the practice of the invention are expected to occur to those skilled in the art upon consideration of the foregoing description of the presently preferred embodiments thereof.

What is claimed is:

1. A method for treating injury or degeneration of cells of the inner ear comprising administering to a subject a therapeutically effective amount of a neurturin protein product comprising an amino acid sequence set forth in SEQ ID NOs: 1, 2, 3, 4 or 5 wherein said neurturin protein product promotes the survival or function of cochlear hair cells and auditory neurons of the inner ear.

2. The method of claim 1, wherein the hearing loss is associated with injury or degeneration of neuroepithelial hair cells in the inner ear.

3. The method of claim 1, wherein the hearing loss is associated with injury or degeneration of spiral ganglion neurons.

4. The method of claim 1, wherein said auditory neurons are spiral ganglion neurons.

5. The method of claim 1, wherein the neurturin protein product has the amino acid sequence set forth in SEQ ID NO:1.

6. The method of claim 1, wherein the neurturin protein product has the amino acid sequence set forth in SEQ ID NOs:3 and 4.

7. The method of claim 1, wherein the neurturin protein product is (Met$^{-1}$)neurturin.

8. The method of claim 1, wherein the neurturin protein product is administered at a dose of about 1 µg/kg/day to about 100 mg/kg/day.

9. The method of claim 1, wherein the neurturin protein product is administered by cell therapy or gene therapy means wherein cells have been modified to produce and secrete the neurturin protein product.

10. The method of claim 8, wherein the cells have been modified ex vivo.

11. The method of claim 8, wherein the cells have been modified in vivo.

* * * * *

UNITED STATES PATENT AND TRADEMARK OFFICE
CERTIFICATE OF CORRECTION

PATENT NO. : 6,043,221
DATED : March 28, 2000
INVENTOR(S) : Ella Magal and John M. Delaney It is certified that error appears in the above-identified patent and that said Letters Patent is hereby corrected as shown below:

Column 37, Line 47, change "poly-L-omithine" to --poly-L-ornithine--.

Column 37, Line 50, change "polyomithine" to --polyornithine--.

Column 37, Line 65, add --30-- before "cochlea".

Column 42, Line 21-22, change "from to 50%" to --from 20 to 50%--.

Signed and Sealed this

Fifteenth Day of May, 2001

*Attest:*

NICHOLAS P. GODICI

*Attesting Officer*   Acting Director of the United States Patent and Trademark Office

```
                          SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
         (A) LENGTH: 102 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:1:

Ala Arg Leu Gly Ala Arg Pro Cys Gly Leu Arg Glu Leu Glu Val Arg
1               5                   10                  15

Val Ser Glu Leu Gly Leu Gly Tyr Ala Ser Asp Glu Thr Val Leu Phe
            20                  25                  30

Arg Tyr Cys Ala Gly Ala Cys Glu Ala Ala Ala Arg Val Tyr Asp Leu
        35                  40                  45

Gly Leu Arg Arg Leu Arg Gln Arg Arg Arg Leu Arg Arg Glu Arg Val
50                  55                  60

Arg Ala Gln Pro Cys Cys Arg Pro Thr Ala Tyr Glu Asp Glu Val Ser
65                  70                  75                  80

Phe Leu Asp Ala His Ser Arg Tyr His Thr Val His Glu Leu Ser Ala
                85                  90                  95

Arg Glu Cys Ala Cys Val
            100

(2) INFORMATION FOR SEQ ID NO:2:

(i) SEQUENCE CHARACTERISTICS:
         (A) LENGTH: 100 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:2:

Pro Gly Ala Arg Pro Cys Gly Leu Arg Glu Leu Glu Val Arg Val Ser
1               5                   10                  15

Glu Leu Gly Leu Gly Tyr Thr Ser Asp Glu Thr Val Leu Phe Arg Tyr
            20                  25                  30

Cys Ala Gly Ala Cys Glu Ala Ala Ile Arg Ile Tyr Asp Leu Gly Leu
        35                  40                  45

Arg Arg Leu Arg Gln Arg Arg Arg Val Arg Arg Glu Arg Ala Arg Ala
```

```
                50                  55                  60
His Pro Cys Cys Arg Pro Thr Ala Tyr Glu Asp Glu Val Ser Phe Leu
 65                  70                  75                  80

Asp Val His Ser Arg Tyr His Thr Leu Gln Glu Leu Ser Ala Arg Glu
                 85                  90                  95

Cys Ala Cys Val
            100
```

(2) INFORMATION FOR SEQ ID NO:3:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..309

(xi) SEQUENCE DESCRIPTION: SEQ ID NO:3:

```
ATG GCA CGT CTG GGT GCT CGT CCG TGT GGT CTG CGT GAA CTG GAA GTT        48
Met Ala Arg Leu Gly Ala Arg Pro Cys Gly Leu Arg Glu Leu Glu Val
 1               5                  10                  15

CGT GTT TCC GAA CTG GGT CTG GGT TAC GCT TCC GAC GAA ACC GTT CTG        96
Arg Val Ser Glu Leu Gly Leu Gly Tyr Ala Ser Asp Glu Thr Val Leu
                20                  25                  30

TTC CGT TAC TGT GCA GGT GCT TGT GAA GCA GCT GCA CGT GTT TAC GAC       144
Phe Arg Tyr Cys Ala Gly Ala Cys Glu Ala Ala Ala Arg Val Tyr Asp
             35                  40                  45

CTG GGT CTG CGT CGC CTG CGT CAG CGC CGT CGC CTG CGT CGC GAA CGT       192
Leu Gly Leu Arg Arg Leu Arg Gln Arg Arg Leu Arg Arg Glu Arg
         50                  55                  60

GTT CGC GCA CAG CCG TGT TGC CGT CCG ACC GCA TAC GAA GAC GAA GTT       240
Val Arg Ala Gln Pro Cys Cys Arg Pro Thr Ala Tyr Glu Asp Glu Val
 65                  70                  75                  80

TCC TTC CTG GAC GCT CAC TCC CGT TAC CAC ACC GTT CAC GAA CTG TCC       288
Ser Phe Leu Asp Ala His Ser Arg Tyr His Thr Val His Glu Leu Ser
                 85                  90                  95

GCA CGT CAC TGT GCG TGT GTT TAA                                       312
Ala Arg His Cys Ala Cys Val
            100
```

(2) INFORMATION FOR SEQ ID NO:4:

(i) SEQUENCE CHARACTERISTICS:
        (A) LENGTH: 103 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Arg Leu Gly Ala Arg Pro Cys Gly Leu Arg Glu Leu Glu Val
 1               5                  10                  15

Arg Val Ser Glu Leu Gly Leu Gly Tyr Ala Ser Asp Glu Thr Val Leu
                20                  25                  30

Phe Arg Tyr Cys Ala Gly Ala Cys Glu Ala Ala Ala Arg Val Tyr Asp
             35                  40                  45

Leu Gly Leu Arg Arg Leu Arg Gln Arg Arg Leu Arg Arg Glu Arg
         50                  55                  60
```

-continued

```
Val Arg Ala Gln Pro Cys Cys Arg Pro Thr Ala Tyr Glu Asp Glu Val
 65                  70                  75                  80

Ser Phe Leu Asp Ala His Ser Arg Tyr His Thr Val His Glu Leu Ser
                 85                  90                  95

Ala Arg His Cys Ala Cys Val
                100
```

(2) INFORMATION FOR SEQ ID NO:5:

(i) SEQUENCE CHARACTERISTICS:
        (A) LENGTH: 197 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Gln Arg Trp Lys Ala Ala Leu Ala Ser Val Leu Cys Ser Ser
 1               5                  10                  15

Val Leu Ser Ile Trp Met Cys Arg Glu Gly Leu Leu Leu Ser His Arg
                 20                  25                  30

Leu Gly Pro Ala Leu Val Pro Leu His Arg Leu Pro Arg Thr Leu Asp
                 35                  40                  45

Ala Arg Ile Ala Arg Leu Ala Gln Tyr Arg Ala Leu Leu Gln Gly Ala
             50                  55                  60

Pro Asp Ala Met Glu Leu Arg Glu Leu Thr Pro Trp Ala Gly Arg Pro
 65                  70                  75                  80

Pro Gly Pro Arg Arg Arg Ala Gly Pro Arg Arg Arg Arg Ala Arg Ala
                 85                  90                  95

Arg Leu Gly Ala Arg Pro Cys Gly Leu Arg Glu Leu Glu Val Arg Val
                100                 105                 110

Ser Glu Leu Gly Leu Gly Tyr Ala Ser Asp Glu Thr Val Leu Phe Arg
             115                 120                 125

Tyr Cys Ala Gly Ala Cys Glu Ala Ala Ala Arg Val Tyr Asp Leu Gly
             130                 135                 140

Leu Arg Arg Leu Arg Gln Arg Arg Arg Leu Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
                180                 185                 190

Glu Cys Ala Cys Val
            195
```